(12) United States Patent
Hayakawa et al.

(10) Patent No.: US 7,958,789 B2
(45) Date of Patent: Jun. 14, 2011

(54) CAPACITIVE SENSOR

(75) Inventors: Tomonori Hayakawa, Komaki (JP);
Ayumu Kida, Nagoya (JP); Jun Kobayashi, Komaki (JP); Kazunobu Hashimoto, Nagoya (JP)

(73) Assignee: Tokai Rubber Industries, Ltd., Komaki-Shi (JP)

( * ) Notice: Subject to any disclaimer, the term of this patent is extended or adjusted under 35 U.S.C. 154(b) by 168 days.

(21) Appl. No.: 12/535,150

(22) Filed: Aug. 4, 2009

(65) Prior Publication Data
US 2010/0033196 A1 Feb. 11, 2010

(30) Foreign Application Priority Data

Aug. 8, 2008 (JP) .................................. 2008-206410
Aug. 8, 2008 (JP) .................................. 2008-206413

(51) Int. Cl.
G01L 1/12 (2006.01)
(52) U.S. Cl. ..................................... 73/862.626; 73/780
(58) Field of Classification Search .................... 73/780, 73/862.626
See application file for complete search history.

(56) References Cited

U.S. PATENT DOCUMENTS

| 6,450,026 | B1 * | 9/2002 | Desarnaud | ................. 73/335.04 |
| 6,791,342 | B2 | 9/2004 | Ono | |
| 6,847,527 | B2 * | 1/2005 | Sylvester et al. | ............. 361/763 |
| 7,132,642 | B2 * | 11/2006 | Shank et al. | .................. 250/221 |
| 7,317,392 | B2 * | 1/2008 | DuRocher | ..................... 340/562 |
| 7,391,411 | B2 | 6/2008 | Morimoto et al. | |
| 7,437,953 | B2 * | 10/2008 | DeConde et al. | ........ 73/862.042 |
| 7,563,393 | B2 * | 7/2009 | Hayakawa et al. | ........... 252/500 |
| 7,694,582 | B2 * | 4/2010 | Hayakawa et al. | ............. 73/849 |
| 7,703,333 | B2 * | 4/2010 | Hayakawa et al. | ............. 73/849 |
| 2004/0170006 | A9 * | 9/2004 | Sylvester et al. | ............. 361/794 |
| 2009/0015270 | A1 * | 1/2009 | Hayakawa et al. | ........... 324/686 |

FOREIGN PATENT DOCUMENTS

| JP | B-50-19057 | 7/1975 |
| JP | A-61-210686 | 9/1986 |
| JP | A-62-226030 | 10/1987 |
| JP | H03-53258 U | 5/1991 |
| JP | A-5-288619 | 11/1993 |
| JP | A-11-132879 | 5/1999 |
| JP | A-2004-117042 | 4/2004 |
| JP | A-2005-315831 | 11/2005 |

* cited by examiner

*Primary Examiner* — Max Noori
(74) *Attorney, Agent, or Firm* — Oliff & Berridge, PLC

(57) ABSTRACT

A capacitive sensor includes a dielectric layer made of an elastomer and a pair of electrodes arranged via the dielectric layer, and detects deformation on the basis of electrostatic capacity variation between the pair of electrodes. The pair of electrodes contain an elastomer and conductive fillers filled into the elastomer, are expandable and contractible in accordance with deformation of the dielectric layer, and exhibit little conductivity variation even when the pair of electrodes expand and contract. At least one of the dielectric layer and the electrodes is formed by a printing method using a dielectric layer coating containing a formation component of the dielectric layer or an electrode coating containing a formation component of the electrode.

14 Claims, 15 Drawing Sheets

CAPACITIVE SENSOR

INCORPORATION BY REFERENCE

This application is based on and claims priority under 35 U.S.C. 119 with respect to Japanese Patent Application Nos. 2008-206410 and 2008-206413, both of which were filed on Aug. 8, 2008, and the entire content of which is incorporated herein by reference.

BACKGROUND OF THE INVENTION

1. Field of the Invention

The present invention relates to a capacitive sensor that detects deformation and the like on the basis of electrostatic capacity variation between electrodes.

2. Description of the Related Art

With a capacitive sensor, compressive deformation can be detected using variation in electrostatic capacity accompanying variation in the distance between a pair of electrodes. For example, Japanese Patent Application Publication No. JP-05-288619-A and Japanese Patent Application Publication No. JP-2004-117042-A disclose capacitive sensors including a pair of electrodes that face each other via a space. Further, Japanese Patent Application Publication No. JP-2005-315831-A discloses a capacitive sensor in which electrodes, each of which is constituted by a conductive fabric, are arranged on both surfaces of a sheet dielectric body.

A metallic material is used for the electrodes of the capacitive sensor described in Japanese Patent Application Publication No. JP-05-288619-A. A metallic electrode is not stretchable. Therefore, when the electrode bends, for example, the electrode is likely to break due to plastic deformation. Further, when a capacitive sensor is configured such that a dielectric body, which is elastically deformable, is interposed between metallic electrodes, the dielectric body is bendable, but the electrodes cannot follow the deformation of the dielectric body. Therefore, the electrodes peel away from the dielectric body and cannot be used repeatedly. Hence, a capacitive sensor having metallic electrodes is not suitable for detecting bending deformation. In addition, attachment thereof to a curved surface is difficult.

Japanese Patent Application Publication No. JP-2004-117042-A states that the electrodes may be formed from a material other than metal. More specifically, according to the capacitive sensor described in Japanese Patent Application Publication No. JP-2004-117042-A, one of the electrodes is formed from conductive rubber and the other electrode is formed from conductive ink using a screen printing method.

However, in the capacitive sensors of both Japanese Patent Application Publication No. JP-05-288619-A and Japanese Patent Application Publication No. JP-2004-117042-A, an air layer is provided between the pair of electrodes. The electrostatic capacity (capacitance) of a capacitive sensor in which a dielectric layer is interposed between a pair of electrodes can typically be determined using the following Equation (1).

$$C = \epsilon_0 \epsilon_r S/d \quad (1)$$

[C: capacitance, $\epsilon_0$: dielectric constant in a vacuum, $\epsilon_r$: specific dielectric constant of the dielectric layer, S: electrode area, d: distance between electrodes]

As apparent from Equation (1), the capacitance (C) increases as the electrode area (S) increases with respect to a strain inputted from outside. Further, when the thickness of the dielectric layer, or in other words the distance between electrodes (d), decreases, the capacitance (C) increases. Here, as the specific dielectric constant ($\epsilon_r$) of the dielectric layer becomes large, the capacitance (C) output from the capacitive sensor increases. In other words, variation in the capacitance (C) between before and after a load is applied from the measurement subject to the capacitive sensor becomes larger.

However, in the capacitive sensors of Japanese Patent Application Publication No. JP-05-288619-A and Japanese Patent Application Publication No. JP-2004-117042-A, the specific dielectric constant of the air layer is small. Therefore, the detected electrostatic capacity is small. In other words, the detection sensitivity is low. Moreover, a high degree of dimensional precision of the distance between electrodes is required, and therefore manufacturing cost is high.

Meanwhile, in the capacitive sensor described in Japanese Patent Application Publication No. JP-2005-315831-A, a fabric that is electrically conductive (a conductive fabric) is used for the electrodes. The conductive fabric is stretchable. However, the stretching direction is limited by the weave. Furthermore, the conductive fabric takes a mesh form, and therefore the electrode area decreases in accordance with the gaps in the mesh, leading to a reduction in the electrostatic capacity.

Further, Japanese Patent Application Publication No. JP-05-288619-A discloses a sensor sheet over which a large number of sensor cells (capacitive sensors) are dispersed. When a load is applied to the sensor cells from the measurement subject, the thickness of the air layer varies. When the thickness of the air layer varies, the electrostatic capacity between the pair of electrodes varies. On the basis of this electrostatic capacity variation, the sensor sheet detects irregular forms and the like on the measurement subject as a surface pressure distribution. However, in the sensor sheet disclosed in Japanese Patent Application Publication No. JP-05-288619-A, one sensor cell is arranged in each of the portions in which the surface pressure is to be detected. Therefore, the number of sensor cells, and accordingly the number of electrodes, is large. Moreover, since the number of electrodes is large, a large number of conductors are required to detect the electrostatic capacity.

SUMMARY OF THE INVENTION

The present invention has been designed in consideration of the circumstances described above, and it is a first object of the present invention to provide a capacitive sensor that possesses stretching flexibility, is capable of detecting deformation such as bending, and is suitable for mass production, and on which sensor components can be integrated easily. Further, it is a second object of the present invention to provide a capacitive sensor that possesses stretching flexibility, is capable of detecting a surface pressure distribution, and exhibits great electrostatic capacity variation, and includes a smaller number of electrodes.

(1) To achieve the first object described above, a capacitive sensor according to a first aspect of the present invention includes a dielectric layer made of an elastomer and a pair of electrodes arranged via the dielectric layer, and detects a deformation on the basis of an electrostatic capacity variation between the pair of electrodes. In the capacitive sensor, the pair of electrodes contain an elastomer and conductive fillers filled into the elastomer, are expandable and contractible in accordance with a deformation of the dielectric layer, and exhibit little conductivity variation when the pair of electrodes expand and contract, and at least one of the dielectric layer and the electrodes is formed by a printing method using a dielectric layer coating containing a formation component of the dielectric layer or an electrode coating containing a formation component of the electrode.

In the capacitive sensor according to the first aspect of the present invention, the elastomer dielectric layer is arranged between the pair of electrodes. A specific dielectric constant of the elastomer is greater than the specific dielectric constant ($\in_r \approx 1$) of air. In other words, in Equation (1), $\in_r$ becomes large. Therefore, in comparison with a sensor in which the pair of electrodes are simply arranged so as to face each other via a space, the capacitance (C) increases, enabling an improvement in detection sensitivity. In addition, since the elastomer dielectric layer is interposed between the electrodes, positioning of the electrodes and adjustment of the distance between electrodes can be performed easily.

Further, the pair of electrodes have an elastomer as a base material, and are therefore flexible and can deform integrally with the dielectric layer. In other words, even when the dielectric layer elongates or bends, the electrodes can deform in accordance with the deformation of the dielectric layer. In this specification, the term "deformation" includes all types of deformation due to compression, elongation, bending, and so on. By making the electrodes expandable and contractible in accordance with deformation of the dielectric layer in this manner, the capacitive sensor according to the first aspect of the present invention can be attached easily to a curved surface. Moreover, the electrode is unlikely to peel away from the dielectric layer even after repeated use. Hence, the capacitive sensor according to the first aspect of the present invention exhibits superior durability.

Furthermore, since the pair of electrodes have an elastomer as a base material, they are denser than electrodes made of fabric. Moreover, a conductive path is formed by conductive fillers to be described below, and therefore the electrodes exhibit favorable conductivity, and the conductivity thereof varies little even when the electrodes expand and contract. Hence, even when the deformation amount of the dielectric layer is large, the electrode function is unlikely to deteriorate.

Furthermore, both the dielectric layer and the electrodes are constituted by elastomers, and therefore the entire sensor is flexible, has good workability, and exhibits a high degree of freedom of shape design. Hence, the capacitive sensor according to the first aspect of the present invention can be used widely as a soft sensor. Moreover, since the sensor is flexible, it can respond easily to a large amount of deformation. Furthermore, by adjusting Young's modulus of the dielectric layer in accordance with the application, the detection sensitivity and the detection range can be adjusted.

In the capacitive sensor according to the first aspect of the present invention, at least one of the dielectric layer and the electrodes is formed using a printing method. In other words, the dielectric layer and the electrodes can be formed simply by printing coatings containing the respective formation components of the dielectric layer and the electrodes. Hence, the capacitive sensor according to the first aspect of the present invention can be manufactured easily and at low cost. Moreover, the dielectric layer and the electrodes can be integrated easily, and are therefore suitable for mass production. Furthermore, by employing a printing method, the freedom of shape can be improved. For example, it becomes easy to reduce the film thickness.

(2) The constitution described in (1) may preferably further include stretchable conductors connected respectively to the pair of electrodes, wherein each of the conductors contains an elastomer and conductive particles filled into the elastomer, has a smaller electric resistance than the electric resistance of the electrodes, and is formed by the printing method using a conductor coating containing a formation component of the conductor.

According to this constitution, the conductors connected respectively to the pair of electrodes also have an elastomer as a base material. Therefore, the conductors are flexible and stretchable. Hence, the conductors can also be deformed in accordance with deformation of the capacitive sensor. Further, the capacitive sensor according to this constitution can be attached easily to a curved surface. Moreover, the electric resistance of the conductors is smaller than that of the electrodes. Hence, electric resistance variation due to the length of the conductors is small. As a result, the detection precision can be maintained even when the length of the conductors increases.

Here, the conductors are formed by a printing method. Therefore, the capacitive sensor according to this constitution can be manufactured easily and at low cost. Furthermore, integration of the conductors with the dielectric layer and the electrodes can be performed easily, thereby facilitating mass production. Moreover, similarly to the dielectric layer and so on, by employing a printing method, the freedom of shape can be improved. For example, it becomes easy to reduce the film thickness.

(3) In the constitution described in (2), the pair of electrodes and the conductors may be preferably printed onto a surface and a back of the dielectric layer.

When the electrodes and the conductors are respectively printed onto the surface and the back of the dielectric layer, the dielectric layer, the electrodes, and the conductors can be integrated easily. Further, the electrodes and the conductors can be positioned easily, thereby facilitating manufacture. Moreover, in comparison with a case in which the dielectric layer, the electrode, and so on are printed onto the surface of a substrate or the like, the number of components can be reduced. Hence, this constitution is employed favorably to reduce the film thickness of the capacitive sensor. In addition, according to this constitution, the manufacturing cost can be reduced.

(4) The constitution described in (2) may preferably further include an insulating layer that is arranged to cover at least one of the electrodes and the corresponding one of the conductors to insulate the electrode and the conductor from the outside.

By disposing the insulating layer, conduction from the electrode and the conductor can be blocked. Hence, according to this constitution, the safety of the capacitive sensor can be improved.

(5) The constitution described in (2) may preferably further include a pair of elastic substrates arranged via the dielectric layer, wherein the electrode that contacts a surface of the dielectric layer and the corresponding conductor are printed onto a back of one of the elastic substrates, and the electrode that contacts a back of the dielectric layer and the corresponding conductor are printed onto a surface of the other elastic substrate.

When the dielectric layer is constituted by a foamed elastomer body, for example, it is difficult to print the electrode and the conductor directly onto the surface and the back of the dielectric layer. According to this constitution, the electrode and the conductor are formed by a printing method and then respectively arranged on the surface and the back of the dielectric layer, without direct printing onto the dielectric layer. Hence, according to this constitution, a flexible and thin capacitive sensor can be constructed easily, regardless of the material of the dielectric layer.

(6) In the constitution described in (1), the pair of electrodes may be preferably constituted by an elastomer composition containing the elastomer and the conductive fillers, and in a percolation curve expressing a relationship between a blended amount of the conductive fillers and an electric resistance in the elastomer composition, the blended amount (critical volume fraction: φc) of the conductive fillers at a first polarity change point at which the electric resistance decreases to cause a transition between insulator and conductor is 25 vol % or less.

Typically, when an elastomer composition is formed by blending conductive fillers with an insulating elastomer, the electric resistance of the elastomer composition varies according to the blended amount of the conductive fillers. FIG. 1 shows an outline of a relationship between the blended amount of the conductive fillers and the electric resistance in the elastomer composition.

As shown in FIG. 1, when conductive fillers 102 are mixed into an elastomer 101, the electric resistance of the elastomer composition is initially substantially identical to the electric resistance of the elastomer 101. However, when the blended amount of the conductive fillers 102 reaches a certain volume fraction, the electric resistance decreases rapidly such that insulator-conductor transition occurs (first polarity change point). The blended amount of the conductive fillers 102 at the first polarity change point will be referred to as the critical volume fraction (φc). When more of the conductive fillers 102 is intermixed, electric resistance variation decreases from a certain volume fraction, leading to saturation of the electric resistance variation (second polarity change point). The blended amount of the conductive fillers 102 at the second polarity change point will be referred to as a saturated volume fraction (φs). This variation in the electric resistance is known as a percolation curve, and is believed to be caused when the conductive fillers 102 form a conducting path PI through the elastomer 101.

For example, when primary particles of the conductive fillers aggregate such that secondary particulation progresses, a conducting path is formed easily by a three-dimensional network structure. In this case, the critical volume fraction (φc) of the elastomer composition is, at approximately 20 vol %, comparatively small. In other words, when the critical volume fraction (φc) is small, the conductive fillers are likely to form a structural secondary aggregate. Hence, an elastomer composition exhibiting high conductivity can be obtained even with a comparatively small blended amount of the conductive fillers.

According to this constitution, the pair of electrodes are constituted by an elastomer composition having a critical volume fraction (φc) of 25 vol % or less. Since the critical volume fraction (φc) is comparatively small, the conductive filer forms an aggregate easily. Hence, an electrode exhibiting favorable conductivity can be obtained using a comparatively small amount of conductive fillers. Note that in this specification, the term "elastomer composition" includes the mixture of an elastomer, conductive fillers, other additives, and so on, in addition to the mixture of an elastomer and conductive fillers.

(7) In the constitution described in (1), the conductive fillers constituting the pair of electrodes may be preferably formed from a carbon material.

Carbon materials are highly conductive and comparatively cheap. Therefore, by using conductive fillers constituted by a carbon material, the manufacturing cost of the capacitive sensor can be reduced.

(8) To achieve the second object described above, a capacitive sensor according to a second aspect of the present invention includes an integrally stretchable sensor main body including: a dielectric layer made of an elastomer; at least one belt-shaped surface side electrode provided on a surface side of the dielectric layer, the surface side electrode being formed to include an elastomer and conductive fillers filled into the elastomer and including a surface side connection portion; at least one belt-shaped back side electrode provided on a back side of the dielectric layer, the back side electrode being formed to include an elastomer and conductive fillers filled into the elastomer and including a back side connection portion; a plurality of detection portions formed by an intersection between the surface side electrode and the back side electrode when seen from a surface-back direction; a surface side conductor that is connected to the surface side connection portion, formed to include an elastomer and conductive particles filled into the elastomer, and has a smaller electric resistance than the electric resistance of the surface side electrode; and a back side conductor that is connected to the back side connection portion, formed to include an elastomer and conductive particles filled into the elastomer, and has a smaller electric resistance than the electric resistance of the back side electrode. The capacitive sensor according to the second aspect of the present invention also includes a calculation portion that is electrically connected to the surface side conductor and the back side conductor, separates an electric resistance corresponding to a distance from the surface side connection portion of the surface side electrode to each of the detection portions and the electric resistance corresponding to a distance from the back side connection portion of the back side electrode to each of the detection portions from an impedance detected from the surface side conductor and the back side conductor, extracts an electrostatic capacity of the each detection portion, and calculates a surface pressure distribution on the sensor main body from the electrostatic capacity of the each detection portion.

The capacitive sensor according to the second aspect of the present invention includes a sensor main body and a calculation portion. The sensor main body includes a dielectric layer, a surface side electrode, a back side electrode, detection portions, a surface side conductor, and a back side conductor. The dielectric layer is made of an elastomer Therefore, as described above, the electrostatic capacity is greater than that of a case in which the dielectric layer is constituted by air. More specifically, variation in electrostatic capacity between before and after a load is applied from the measurement subject to the sensor main body (during application of the load) increases.

Further, the surface side electrode and the back side electrode both take a belt shape. Moreover, the detection portions are arranged using an intersecting portion between the surface side electrode and the back side electrode, and therefore the number of arranged electrodes is reduced. Furthermore, the number of conductors for detecting electrostatic capacity from the detection portions is reduced.

Further, the surface side electrode and the back side electrode are formed to include an elastomer and conductive fillers filled into the elastomer, and therefore, when the surface pressure is applied from a measurement subject, the surface side electrode and the back side electrode can expand and contract together with the dielectric layer in accordance with the surface pressure. Hence, the surface side electrode and the back side electrode are unlikely to restrict expansion and contraction of the dielectric layer.

Further, the surface side conductor and the back side conductor are formed to include an elastomer and conductive particles filled into the elastomer, and therefore, when a load is applied from a measurement subject, the surface side conductor and the back side conductor can expand and contract in accordance with the load. Hence, the surface side conductor and the back side conductor are unlikely to restrict expansion and contraction of the dielectric layer.

The electric resistance of an object is derived from the following Equation (2).

$$r = \rho L / S \quad (2)$$

[r: electric resistance, ρ: resistivity, L: length, S: sectional area]

As apparent from Equation (2), the electric resistance r increases as the length L of the object increases. Therefore, the electric resistance increases as the distance from the surface side connection portion of the surface side electrode to the detection portion increases. Likewise, the electric resistance increases as the distance from the back side connection portion of the back side electrode to the detection portion increases. In other words, the electric resistance may differ in each of the plurality of detection portions in accordance with this distance. Hence, when the surface pressure distribution is calculated using the impedance detected from the surface side conductor and the back side conductor as is, the measurement precision of the surface pressure distribution decreases due to the effect of the electric resistance described above.

In the capacitive sensor according to the second aspect of the present invention, however, the electric resistance corresponding to the distance from the surface side connection portion of the surface side electrode to the detection portion and the electric resistance corresponding to the distance from the back side connection portion of the back side electrode to the detection portion axe separated from the impedance detected from the surface side conductor and the back side conductor. In other words, the electrostatic capacity of the detection portion is extracted from the detected impedance. Therefore, the measurement precision of the surface pressure distribution remains high.

(8-1) In the constitution described in (8), the elastomer serving as the material of the dielectric layer may preferably include one or more materials selected from silicone rubber, acrylonitrile-butadiene copolymer rubber, acrylic rubber, epichlorohydrin rubber, chlorosulfonated polyethylene, chlorinated polyethylene, and urethane rubber. According to this constitution, the specific dielectric constant of the dielectric layer is large, enabling an increase in the electrostatic capacity.

(8-2) In the constitution described in (8), at least one of the elastomer serving as the material of the surface side electrode and the elastomer serving as the material of the back side electrode may preferably include one or more materials selected from silicone rubber, ethylene-propylene copolymer rubber, natural rubber, styrene-butadiene copolymer rubber, acrylonitrile-butadiene copolymer rubber, acrylic rubber, epichlorohydrin rubber, chlorosulfonated polyethylene, chlorinated polyethylene, and urethane rubber. According to this constitution, the stretchability of at least one of the surface side electrode and the back side electrode increases. As a result, at least one of the surface side electrode and the back side electrode can easily expand and contract integrally with the dielectric layer.

(8-3) In the constitution described in (8), the conductive fillers included in the surface side electrode and the back side electrode may be preferably non-metallic conductive fillers. According to this constitution, the electric resistance of the surface side electrode and the back side electrode is larger than that of a case in which the surface side electrode and the back side electrode contain metallic conductive fillers. More specifically, the electric resistance corresponding to the distance from the surface side connection portion of the surface side electrode to the detection portion, and the electric resistance corresponding to the distance from the back side connection portion of the back side electrode to the detection portion increase. The electric resistance is separated from the detected impedance, and therefore, according to this constitution, the measurement precision of the surface pressure distribution is high even though the electric resistance of the surface side electrode and the back side electrode is large.

(8-4) In the constitution described in (8-3), the non-metallic conductive fillers may be preferably carbon-based conductive fillers. According to this constitution, the measurement precision of the surface pressure distribution is high even though the electric resistance of the surface side electrode and the back side electrode is large.

(9) In the constitution described in (8), the calculation portion may preferably calculate a total load applied to the sensor main body by integrating the electrostatic capacity of each of the plurality of detection portions. According to this constitution, the total load applied to the sensor main body can be calculated from the electrostatic capacity of each detection portion. As a result, the weight of the measurement subject, for example, can be detected.

(10) In the constitution described in (8), the surface side electrode may be preferably arranged in a plurality of rows, the back side electrode may be preferably arranged in a plurality of rows, and the plurality of surface side electrodes and the plurality of back side electrodes may be arranged substantially orthogonally to each other when seen from the surface-back direction.

According to this constitution, the plurality of detection portions can be dispersed easily over the entire surface of the sensor main body. As a result, of the entire surface of the sensor main body, the surface area of portions in which the surface pressure can be detected can be increased. Further, variation in arrangement of the detection portions over the entire surface of the sensor main body can be suppressed.

(11) In the constitution described in (8), the surface side electrode and the surface side conductor may be preferably printed onto a surface of the dielectric layer, and back side electrode and the back side conductor may be preferably printed onto a back of the dielectric layer.

In other words, in this constitution, the sensor main body is manufactured by printing the surface side electrode, the surface side conductor, the back side electrode, and the back side conductor onto the dielectric layer. According to this constitution, the constitutional elements required to measure the surface pressure, i.e. the dielectric layer, the surface side electrode, the surface side conductor, the back side electrode, and the back side conductor, can be integrated comparatively easily. As a result, the production efficiency of the sensor main body, and therefore the capacitive sensor, is high.

Furthermore, the surface side electrode and the back side electrode are printed directly onto the dielectric layer, and therefore positioning of the surface side electrode and the back side electrode can be performed easily. Hence, the detection portions can be arranged accurately in desired positions.

(12) In the constitution described in (8), the sensor main body may preferably further include: a surface side insulating cover layer that is printed over the surface side electrode and the surface side conductor either directly or indirectly so as to insulate the surface side electrode and the surface side conductor from the outside; and a back side insulating cover layer that is printed over the back side electrode and the back side conductor either directly or indirectly so as to insulate the back side electrode and the back side conductor from the outside.

According to this constitution, conduction between members outside the capacitive sensor, and the surface side electrode and the surface side conductor can be suppressed. Likewise, conduction between the members outside the capacitive sensor, and the back side electrode and the back side conductor can be suppressed.

(13) In the constitution described in (8), the sensor main body may preferably further include a tubular insulating tube member that insulates an interior and an exterior of the insulating tube member, and the dielectric layer may be preferably housed in the insulating tube member. Further, the surface side electrode and the surface side conductor may be preferably printed onto an inner surface of the insulating tube member in a portion facing the surface of the dielectric layer, and the back side electrode and the back side conductor are preferably printed onto the inner surface of the insulating tube member in a portion facing the back of the dielectric layer.

According to this constitution, the constitutional elements required to measure the surface pressure, i.e. the dielectric layer, the surface side electrode, the surface side conductor, the back side electrode, and the back side conductor, are housed inside the insulating tube member. Therefore, conduction between members outside the insulating tube member and the constitutional elements can be suppressed.

(14) In the constitution described in (8), a surface resistance between both longitudinal ends of at least one of the surface side electrode and the back side electrode may be preferably 100 k$\Omega$ or less. Here, the surface resistance between the both longitudinal ends is set at 100 k$\Omega$ or less because, when the surface resistance exceeds 100 k$\Omega$, a current that flows during application of alternating current voltage decreases, leading to a reduction in the impedance measurement precision, and as a result, a margin of error in the electrostatic capacity measurement increases.

(14-1) In the constitution described in (8), at least one of the surface side electrode and the back side electrode may be preferably constituted by the elastomer composition containing the elastomer and the conductive fillers described above, and in the percolation curve expressing the relationship between the blended amount of the conductive fillers and the electric resistance in the elastomer composition, the blended amount (critical volume fraction: $\phi c$) of the conductive fillers at the first polarity change point at which the electric resistance decreases to cause the transition between insulator and conductor is 25 vol % or less.

As described above in (6), when the critical volume fraction ($\phi c$) is small, the conductive fillers are likely to form a structural secondary aggregate. Hence, an elastomer composition exhibiting high conductivity can be obtained even with a comparatively small blended amount of conductive fillers. According to this constitution, at least one of the surface side electrode and the back side electrode is constituted by an elastomer composition having a critical volume fraction ($\phi c$) of 25 vol % or less. Since the critical volume fraction (+c) is comparatively small, the conductive fillers form an aggregate easily. Therefore, an electrode exhibiting favorable conductivity can be obtained using a comparatively small amount of conductive fillers.

(15) In the constitution described in (8), the conductive fillers may be preferably formed from one or more materials selected from conductive carbon black, carbon nanotube, a derivative of carbon nanotube, graphite, and conductive carbon fiber. Of these materials, conductive carbon black, graphite, and conductive carbon fiber exhibit favorable conductivity and are comparatively cheap. Hence, according to this constitution, the manufacturing cost of the capacitive sensor can be reduced.

DETAILED DESCRIPTION OF THE EMBODIMENTS

Figure 1:
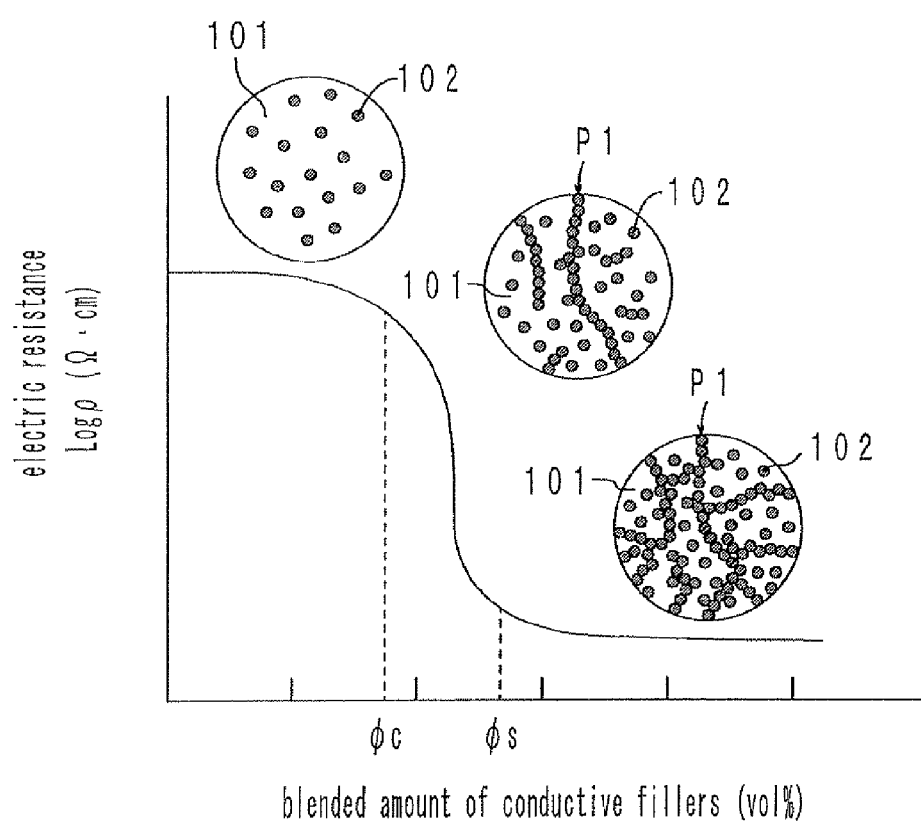
FIG. 1 is a pattern diagram showing a percolation curve in an elastomer composition.

A capacitive sensor according to the present invention may be used for various applications, including, a soft surface pressure sensor for artificial skin or the like, motion capture for detecting human movement, an information input device such as a keyboard, a seating sensor, a collision detection sensor for a vehicle, a surface pressure distribution sensor for a bed or a carpet, and so on. Preferred embodiments of the capacitive sensor according to the present invention will be hereinafter described. First, embodiments of the capacitive sensor according to the first aspect of the present invention (the first capacitive sensor) will be described, followed by embodiments of the capacitive sensor according to the second aspect of the present invention (the second capacitive sensor).

(1) First Capacitive Sensor (Constitution)

The first capacitive sensor according to the present invention includes a dielectric layer made of an elastomer, and a pair of electrodes arranged via the dielectric layer. The elastomer constituting the dielectric layer may be selected appropriately from rubber and a thermoplastic elastomer. The elastomer may also be a foam body. There are no particular limitations on the type of elastomer. For example, an elastomer having large specific dielectric constant is preferable from the viewpoint of increasing the capacitance. The specific dielectric constant at room temperature is preferably 3 or more, and more preferably 5 or more, for example. An elastomer containing a polar functional group such as an ester group, a carboxyl group, a hydroxyl group, a halogen group, an amide group, a sulfone group, a urethane group, or a nitrile group, or an elastomer to which a polar low molecular weight compound containing these polar functional groups is added, for example, may be employed favorably. The elastomer may be crosslinked or not crosslinked. Further, by adjusting the Young's modulus of the elastomer, the detection sensitivity and the detection range can be adjusted in accordance with the application. For example, by employing a foam body having a small Young's modulus, small deformation can be detected easily.

Preferred examples of the elastomer include silicone rubber, acrylonitrile-butadiene copolymer rubber, acrylic rubber, epichlorohydrin rubber, chlorosulfonated polyethylene, chlorinated polyethylene, and urethane rubber.

There are no particular limitations on the thickness of the dielectric layer. For example, the thickness of the dielectric layer is preferably set at 1 μm or more and 5000 μm or less from the viewpoints of reducing the size of the sensor and improving the detection sensitivity by increasing the capacitance in proportion to an inverse of the thickness of the dielectric layer (i.e. the distance between electrodes). A thickness of 20 μm or more and 500 μm or less is more preferable.

The pair of electrodes are respectively arranged on a surface and a back of the dielectric layer. The elastomer constituting the electrodes may be the same as the elastomer used for the dielectric layer, or may be different. When the electrodes and the dielectric layer are constituted by the identical elastomer, the ability of the electrodes to follow deformation of the dielectric layer is improved. Furthermore, adhesiveness between the dielectric layer and the electrodes is improved, and therefore the electrodes are less likely to peel away from the dielectric layer despite cyclic fatigue, leading to an improvement in reliability.

The electrode elastomer preferably has a critical volume fraction ($\phi$c) of 25 vol % or less in a percolation curve when a mixture (elastomer composition) of the elastomer and conductive fillers is prepared. When the critical volume fraction ($\phi$c) is 25 vol % or less, an electrode that possesses high conductivity can be obtained even when the amount of blended conductive fillers is comparatively small.

Elastomers that are suitably used for the electrode include silicone rubber, ethylene-propylene copolymer rubber, natural rubber, styrene-butadiene copolymer rubber, acrylonitrile-butadiene copolymer rubber, acrylic rubber, epichlorohydrin rubber, chlorosulfonated polyethylene, chlorinated polyethylene, and urethane rubber.

Examples of the conductive fillers blended with the elastomer may include a carbon material and a metal. One of these materials may be used individually, or two or more of the materials may be mixed, as the conductive fillers. For example, a carbon material is preferably used due to its comparatively low cost and the ease to form a conductive path. Carbon black exhibiting superior conductivity, such as ketjen black, for example, is preferable as the carbon material since such type of carbon black has a small particle diameter and aggregates easily.

There are no particular limitations on the shape of the conductive fillers, and the conductive fillers may have a spherical shape, a needle shape, a square column shape, and so on. An aspect ratio (the ratio of a long side to a short side) of the conductive fillers is preferably 1 or more, for example. When needle-shaped conductive fillers having a comparatively large aspect ratio are used, for example, a three-dimensional conductive network can be formed easily, and therefore high conductivity can be realized with a small amount of the fillers. Moreover, conductivity variation during expansion and contraction of the electrode can be suppressed.

Further, an average particle diameter, compatibility with the elastomer, and so on may be taken into consideration when selecting the conductive fillers. For example, when spherical conductive fillers are employed, the average particle diameter (primary particle) of the conductive fillers is preferably 0.01 μm or more and 0.5 μm or less. When the average particle diameter is smaller than 0.01 μm, the cohesiveness of the fillers is high, and therefore the fillers cannot easily be dispersed evenly when a coating is prepared. Hence, the average particle diameter is preferably 0.03 μm or more. Conversely, when the average particle diameter exceeds 0.5 μm, it becomes difficult to form an aggregate (a secondary particle). Hence, the average particle diameter is preferably 0.1 μm or less. Note that the critical volume fraction ($\phi$c) in a percolation curve can be adjusted within a desired range by appropriately adjusting the combination of the conductive fillers and the elastomer, the average particle diameter of the conductive fillers, and so on.

To realize a desired conductivity, the conductive fillers are preferably blended at a ratio of at least the critical volume fraction ($\phi$c) in a percolation curve. On the other hand, when the filling rate of the conductive fillers exceeds 30 vol %, blending with the elastomer becomes difficult, leading to a reduction in moldability and a reduction in stretchability of the electrode Hence, the filling rate of the conductive fillers is preferably 30 vol % or less. Further, to secure stretchability of the electrode, a comparatively small amount of the conductive fillers is preferably blended so as to realize high conductivity. Accordingly, the filling rate of the conductive fillers is preferably set at 25 vol % or less when the volume of the electrode is 100 vol %, and more preferably at 15 vol % or less.

There are no particular limitations on the thickness of the electrode, but the thickness is preferably set at 1 μm or more and 100 μm or less, taking into consideration the ability of the electrode to follow the dielectric layer and in order to reduce the size of the sensor. Further, the Young's modulus of the electrode is preferably 0.1 MPa or more and 10 MPa or less to improve the ability of the electrode to follow deformation of the dielectric layer. Likewise, elongation at break in the tensile test (JIS K6251) is preferably 200% or more.

Further, the electric resistance of the electrode is preferably 100 kΩ or less, and more preferably 10 kΩ or less, in a thickness direction and a surface direction. Here, variation in the conductivity of the electrode remains small even when the electrode expands and contracts. For example, when the electrode is elongated in one direction such that a distance between terminals is extended to 100%, if a resistance across terminals (R1) is 10 times or less a resistance across terminals before elongation (R1/R0≦10), it can be said that "variation in the conductivity of the electrode remains small even when the electrode expands and contracts."

In addition to the elastomer and conductive fillers described above, various additives may be blended in the electrode. Examples of these additives include a crosslinking agent, a vulcanizing accelerator, a vulcanization aid, an age resistor, a plasticizer, a softener, and a colorant.

In the first capacitive sensor according to the present invention, a conductor connected to each of the pair of electrodes is preferably expandable and contractible. In this case, the conductor may be constituted so as to include an elastomer and conductive particles filled into the elastomer, for example.

The elastomer constituting the conductor may be the same as the elastomer used for the dielectric layer and the electrode or may be different. Suitable examples of the elastomer include silicone rubber, ethylene-propylene copolymer rubber, natural rubber, styrene-butadiene copolymer rubber, acrylonitrile-butadiene copolymer rubber, acrylic rubber, epicblorohydrin rubber, chlorosulfonated polyethylene, chlorinated polyethylene, and urethane rubber.

Further, there are no particular limitations on the type of conductive particles constituting the conductor as long as the conductivity thereof is high. For example, metal powder made of silver, gold, copper, nickel, and so on may be employed. Further, in order to realize the desired conductivity, the filling rate of the conductive particles in the elastomer is preferably set at 20 vol % or more when the volume of the conductor is 10 vol %. When the filling rate of the conductive particles exceeds 65 vol %, blending into the elastomer becomes difficult, leading to a reduction in moldability and a reduction in the stretchability of the conductor Hence, the filling rate of the conductive particles is preferably 50 vol % or less.

The first capacitive sensor according to the present invention may include an insulating layer for insulating the electrodes and the conductors from the outside. In this case, the insulating layer may be arranged to cover the electrode and the conductor arranged on at least one of the surface and the back of the dielectric layer. A film that possesses an insulating property and is elastically deformable is preferably employed as the insulating layer. Suitable examples of the insulating layer include silicone rubber, ethylene-propylene copolymer rubber, natural rubber, styrene-butadiene copolymer rubber, acrylonitrile-butadiene copolymer rubber, acrylic rubber, epichlorohydrin rubber, chlorosulfonated polyethylene, chlorinated polyethylene, and urethane rubber.

Further, the first capacitive sensor according to the present invention may be formed by disposing the dielectric layer, the electrodes, and the like on a substrate surface made of other material than an elastomer. A flexible resin film made of polyimide, polyethylene, polyethylene terephthalate (PET), polyethylene naphthalate (PEN), for example, may be used as the substrate. When a flexible resin film is used as the substrate, expansion and contraction of the dielectric layer and so on are restrained by the substrate. This makes it possible to more easily detect bending deformation. Further, stretchable fiber may be used as the substrate. In this case, the sensor itself can be reinforced without inhibiting expansion and contraction of the dielectric layer and so on.

(Manufacturing Method)

In the first capacitive sensor according to the present invention, at least one of the dielectric layer and the electrodes is formed using a printing method. More specifically, a dielectric layer coating containing the formation components of the dielectric layer or an electrode coating containing the formation components of the electrode may be printed onto a formation position of the dielectric layer or the electrode and then dried by heating so as to vaporize a solvent contained in the coating. Further, during the heating, a crosslinking reaction of the elastomer may be advanced simultaneously. Similarly, when the conductor is formed using a printing method, a conductor coating containing the formation components of the conductor may be printed onto a formation position of the conductor and then dried by heating so as to vaporize a solvent contained in the coating. Furthermore, if necessary, the thickness of the formed dielectric layer, electrode, and so on may be increased by applying the coating in multiple layers. Examples of the printing method include screen printing, inkjet printing, flexographic printing, gravure printing, pad printing, and lithography. Of these methods, the screen printing method is preferable, because a highly viscous coating material can be used and it is easy to adjust the thickness of the coated film.

The dielectric layer coating may be prepared by blending the formation components (elastomer, additives, and so on) of the dielectric layer with a solvent. Similarly, the electrode coating and the conductor coating may be prepared by blending the respective formation components thereof with a solvent. A solid concentration of the respective coatings may be adjusted appropriately to achieve a viscosity suitable for the printing method employed.

The following three methods may be given as examples of a manufacturing method for the first capacitive sensor according to the present invention. In a first method, the electrode and the conductor are printed onto each of the surface and the back of the dielectric layer. In this method, first, an elastomer sheet serving as the dielectric layer is prepared. The conductor coating is then printed onto the surface of the sheet, dried, and crosslinked. Next, the electrode coating is printed onto the surface, dried, and crosslinked. If necessary, an insulating layer is formed so as to cover the electrode and the conductor. Next, the sheet is turned over, whereupon the conductor coating and the electrode coating are each printed onto the back of the sheet, dried, and crosslinked in a similar manner. If necessary, an insulating layer is then formed so as to cover the electrode and the conductor.

In a second method, the dielectric layer, the electrode, and the conductor are respectively printed onto the surface of a substrate. In this method, first, the conductor coating is printed onto the surface of the substrate, dried, and crosslinked. Next, the electrode coating is printed onto the surface, dried, and crosslinked. Next, the dielectric layer coating is printed onto a surface of the formed electrode, dried, and crosslinked. Next, the electrode coating is printed onto the surface of the formed dielectric layer, dried, and crosslinked. The conductor coating is then printed so as to connect to the uppermost electrode, dried, and crosslinked. If necessary, an insulating layer is then formed so as to cover the electrode and the conductor that are exposed.

In a third method, an elastic substrate on which the electrode and the conductor are printed in advance is arranged on each of the surface and the back of the dielectric layer. First, two elastic substrates are prepared. An insulating material, such as silicone rubber, ethylene-propylene copolymer rubber, natural rubber, styrene-butadiene copolymer rubber, acrylonitrile-butadiene copolymer rubber, acrylic rubber, epichlorohydrin rubber, chlorosulfonated polyethylene, chlorinated polyethylene, or urethane rubber, may be used favorably as the elastic substrate. The conductor coating and the electrode coating are then printed onto one of the surfaces of each elastic substrate to form the conductor and the electrode. Next, the elastic substrates are stacked onto both surfaces of the dielectric layer such that the formed electrodes contact the surface and the back of the dielectric layer (an elastomer sheet), respectively. More specifically, in a capacitive sensor manufactured using the third method, the pair of elastic substrates are arranged via the dielectric layer such that the electrode and the conductor that contact the surface of the dielectric layer are printed onto the back of one elastic substrate and the electrode and the conductor that contact the back of the dielectric layer are printed onto the surface of the other elastic substrate.

First Embodiment

An embodiment of the first capacitive sensor according to the present invention will be hereinafter described. Note that embodiments of the first capacitive sensor according to the present invention are not limited to this embodiment, and the first capacitive sensor according to the present invention may be implemented in various modified and improved embodiments possible to a person skilled in the art.

Figure 2:
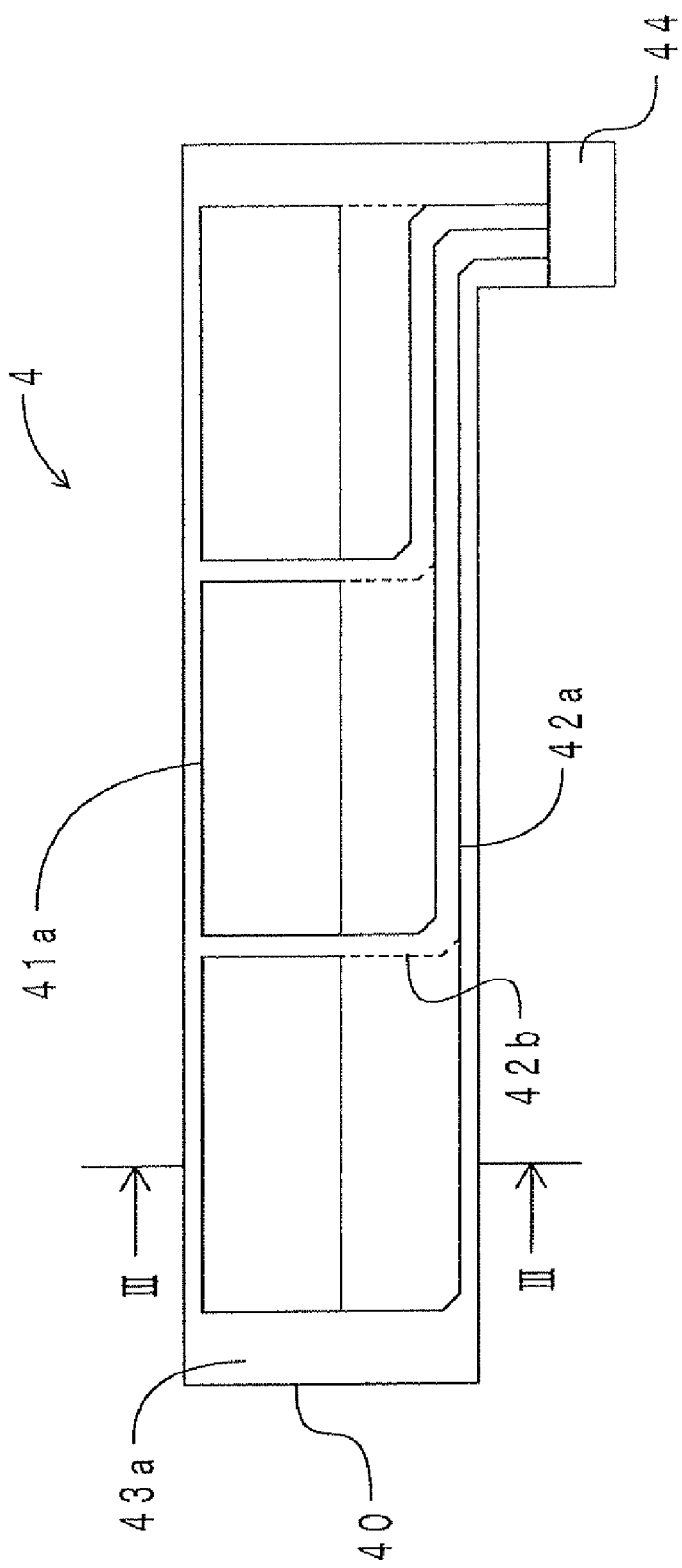
FIG. 2 is a top view of a capacitive sensor according to a first embodiment of the present invention.
Figure 3:
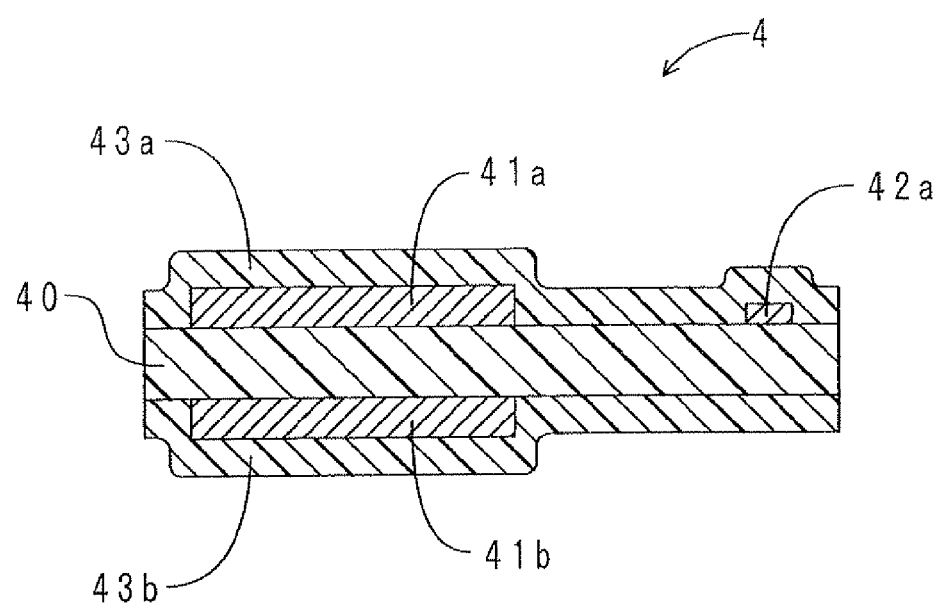
FIG. 3 is a sectional view taken along the line III-III of FIG. 2.

First, the constitution of the capacitive sensor according to this embodiment will be described. FIG. 2 is a top view of the capacitive sensor. FIG. 3 is a sectional view taken along the line III-III of FIG. 2. As shown in FIGS. 2 and 3, a capacitive sensor 4 includes a dielectric layer 40, a pair of electrodes 41a, 41b, conductors 42a, 42b, and cover films 43a, 43b.

The dielectric layer 40 is made from urethane rubber and takes a belt shape extending in a left-right direction. The thickness of the dielectric layer 40 is approximately 300 μm.

The electrode 41a takes a rectangular shape. Three electrodes 41a are formed on an upper surface of the dielectric layer 40 using screen printing. Similarly, the electrode 41b takes a rectangular shape. Three electrodes 41b are formed on a lower surface of the dielectric layer 40 so as to oppose the respective electrodes 41a via the dielectric layer 40. The electrodes 41b are screen-printed onto the lower surface of the dielectric layer 40. Thus, three pairs of the electrodes 41a, 41b are arranged such that the electrodes 41a, 41b sandwich the dielectric layer 40.

The electrodes 41a, 41b are constituted by an elastomer material formed by filling acrylic rubber with ketjen black. The filling rate of the ketjen black in the electrodes 41a, 41b is approximately 15 vol % when the volume of each of the electrodes 41a, 41b is 100 vol %. Further, in a percolation curve of an elastomer composition formed by mixing ketjen black into acrylic rubber, the critical volume fraction ($\phi c$) is approximately 4 vol %, and a saturated volume fraction ($\phi s$) is approximately 15 vol %.

The conductor 42a is connected to each of the electrodes 41a formed on the upper surface of the dielectric layer 40. The electrode 41a is connected to a connector 44 by the conductor 42a. The conductor 42a is formed on the upper surface of the dielectric layer 40 by screen printing. Similarly, the conductor 42b is connected to each of the electrodes 41b formed on the lower surface of the dielectric layer 40 (as shown by broken lines in FIG. 2). The electrode 41b is connected to a connector (not shown) by the conductor 42b. The conductor 42b is formed on the lower surface of the dielectric layer 40 by screen printing. The conductors 42a, 42b are constituted by an elastomer material in which urethane rubber is filled with silver powder.

The cover film 43a is made of acrylic rubber and takes a belt shape extending in the left-right direction. The cover film 43a covers the upper surface of the dielectric layer 40, the electrodes 41a, and the conductor 42a. Similarly, the cover film 43b is made of acrylic rubber and takes a belt shape extending in the left-right direction. The cover film 43b covers the lower surface of the dielectric layer 40, the electrodes 41b, and the conductor 42b. The cover films 43a, 43b are included in an insulating layer according to the present invention.

Next, an operation of the capacitive sensor 4 will be described. When the capacitive sensor 4 is pressed from above, for example, the dielectric layer 40, the electrodes 41a, and the cover film 43a buckle downward integrally. Thus, the thickness of the dielectric layer 40 decreases due to compression. As a result, capacitance between the electrodes 41a, 41b increases. Deformation caused by the compression is detected in accordance with this capacitance variation.

Next, advantageous effects of the capacitive sensor 4 according to this embodiment will be described. According to the capacitive sensor 4 of this embodiment, the dielectric layer 40, the electrodes 41a, 41b, the conductors 42a, 42b, and the cover films 43a, 43b are all constituted by an elastomer material. Therefore, the entire capacitive sensor 4 is flexible, and further, expandable and contractible. Further, when the capacitive sensor 4 deforms due to compression, elongation, and so on, the capacitance varies. The capacitive sensor 4 can detect various types of deformation in accordance with this capacitance variation. Moreover, the freedom of arrangement of the capacitive sensor 4 is high.

The urethane rubber dielectric layer 40 having large specific dielectric constant is interposed between the electrodes 41a, 41b. Therefore, in comparison with a capacitive sensor in which the electrodes 41a, 41b simply face each other via a space, the capacitive sensor 4 exhibits larger capacitance and higher detection sensitivity. Furthermore, the electrodes 41a, 41b are expandable and contractible, and can therefore deform in accordance with deformation of the dielectric layer 40. Hence, the electrodes 41a, 41b are unlikely to peel away from the dielectric layer 40 even when used repeatedly. Accordingly, the capacitive sensor 4 exhibits superior durability. Further, the cover films 43a, 43b are arranged on the uppermost surface, and therefore conduction from the electrodes 41a, 41b and the conductors 42a, 42b can be blocked. As a result, the safety of the capacitive sensor 4 is high.

In the capacitive sensor 4 according to this embodiment, three electrodes 41a and three electrodes 41b are formed to face each other via the dielectric layer 40. However, the number, size, arrangement, and so on of the electrodes may be determined appropriately in accordance with the application.

Second Embodiment

A capacitive sensor according to this embodiment differs from the capacitive sensor according to the first embodiment by the constitution in which the electrodes and the conductors are formed on the elastic substrate, instead of the dielectric layer. Therefore, only this difference will be hereinafter described.

Figure 4:
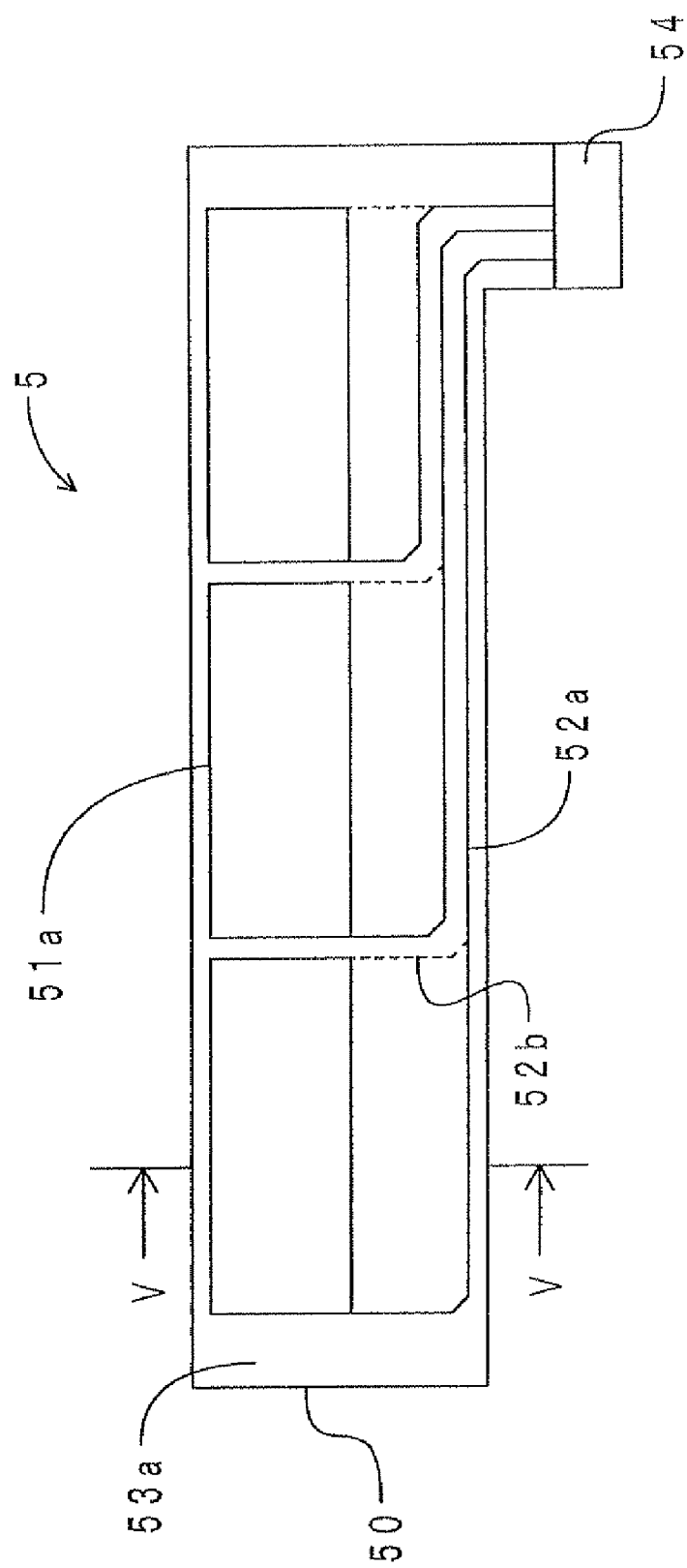
FIG. 4 is a top view of a capacitive sensor according to a second embodiment of the present invention.
Figure 5:
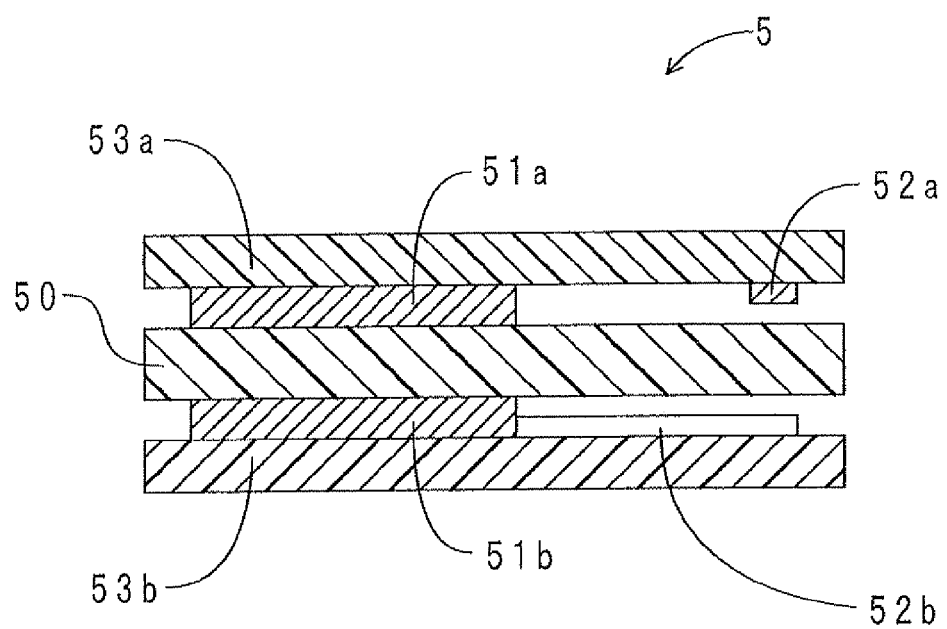
FIG. 5 is a sectional view taken along the line V-V of FIG. 4.

FIG. 4 is a top view of the capacitive sensor according to this embodiment. FIG. 5 is a sectional view taken along the line V-V of FIG. 4. Note that, for ease of description, an upper elastic substrate is shown as being transparent in FIG. 4. Further, in FIG. 5, a gap between the upper elastic substrate and a dielectric layer and a gap between a lower elastic substrate and the dielectric layer are emphasized for ease of description.

As shown in FIGS. 4 and 5, a capacitive sensor 5 includes a dielectric layer 50, a pair of electrodes 51a, 51b, conductors 52a, 52b, an upper elastic substrate 53a, and a lower elastic substrate 53b.

The upper elastic substrate 53a and the lower elastic substrate 53b are made of acrylic rubber and take a belt shape extending in the left-right direction. Three electrodes 51a and three conductors 52a are formed on a lower surface of the upper elastic substrate 53a by screen printing. Each of the electrodes 51a is connected to an upper connector 54 by the corresponding conductor 52a. Three electrodes 51b and three conductors 52b are formed on an upper surface of the lower elastic substrate 53b by screen printing. Each of the electrodes 51b is connected to a lower connector (not shown) by the corresponding conductor 52b.

The dielectric layer 50 is interposed between the upper elastic substrate 53a and the lower elastic substrate 53b. The dielectric layer 50 is made of foamed urethane rubber and takes a belt shape extending in the left-right direction. The thickness of the dielectric layer 50 is approximately 300 μm.

An upper surface of the dielectric layer 50 contacts the electrodes 51a. A lower surface of the dielectric layer 50 contacts the electrodes 51b.

The capacitive sensor 5 according to this embodiment exhibits similar advantageous effects to those of the capacitive sensor according to the first embodiment in relation to portions having common constitutions. Furthermore, according to the capacitive sensor 5 of this embodiment, printing is not performed directly onto the dielectric layer 50. Therefore, a material that is not suitable for printing, such as a foam body, can be used as the dielectric layer 50. Hence, the freedom of material selection of the dielectric layer 50 is improved.

(2) Second Capacitive Sensor

Third Embodiment

[Constitution]

Figure 6:
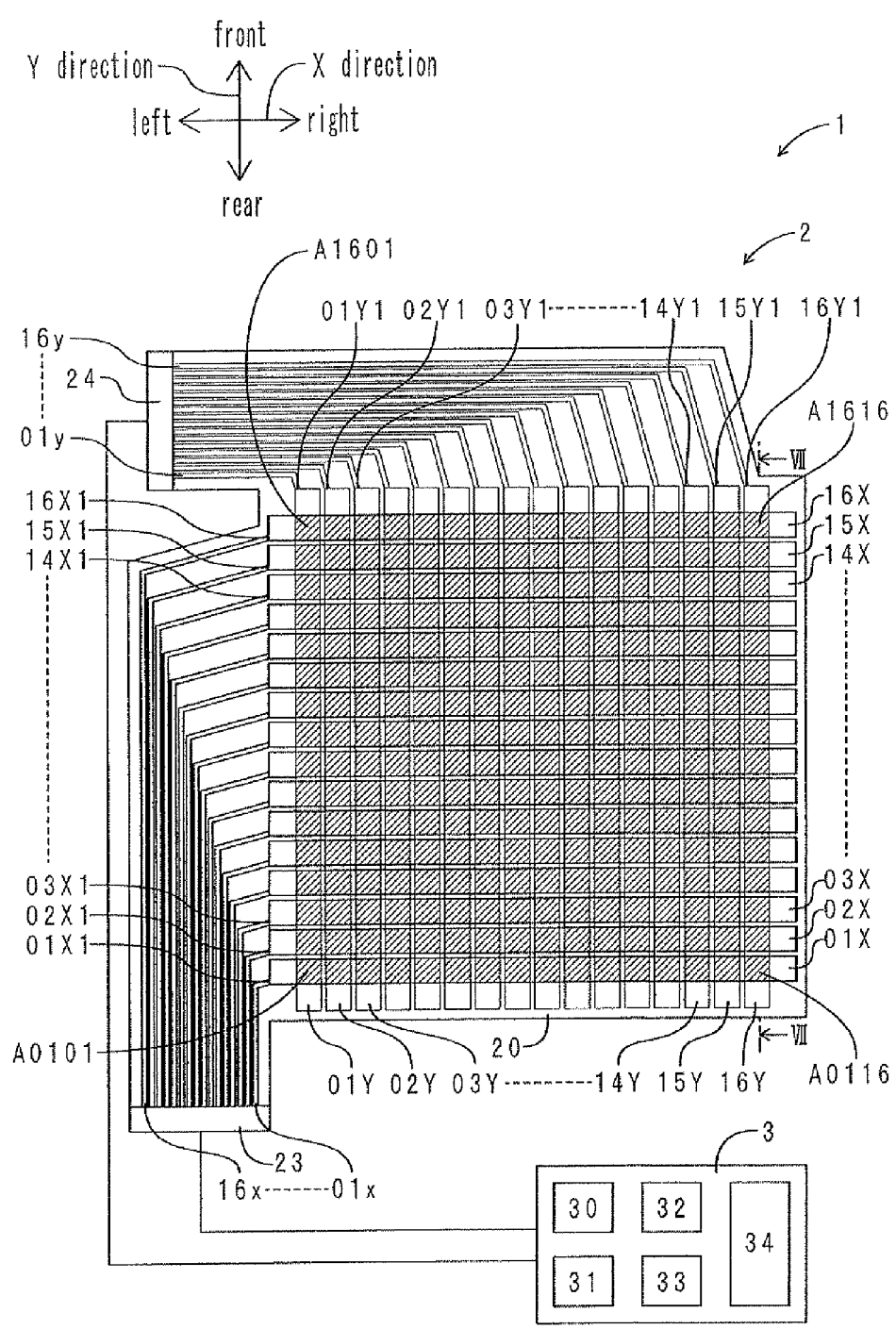
FIG. 6 is a perspective top view of a capacitive sensor according to a third embodiment of the present invention.
Figure 7:
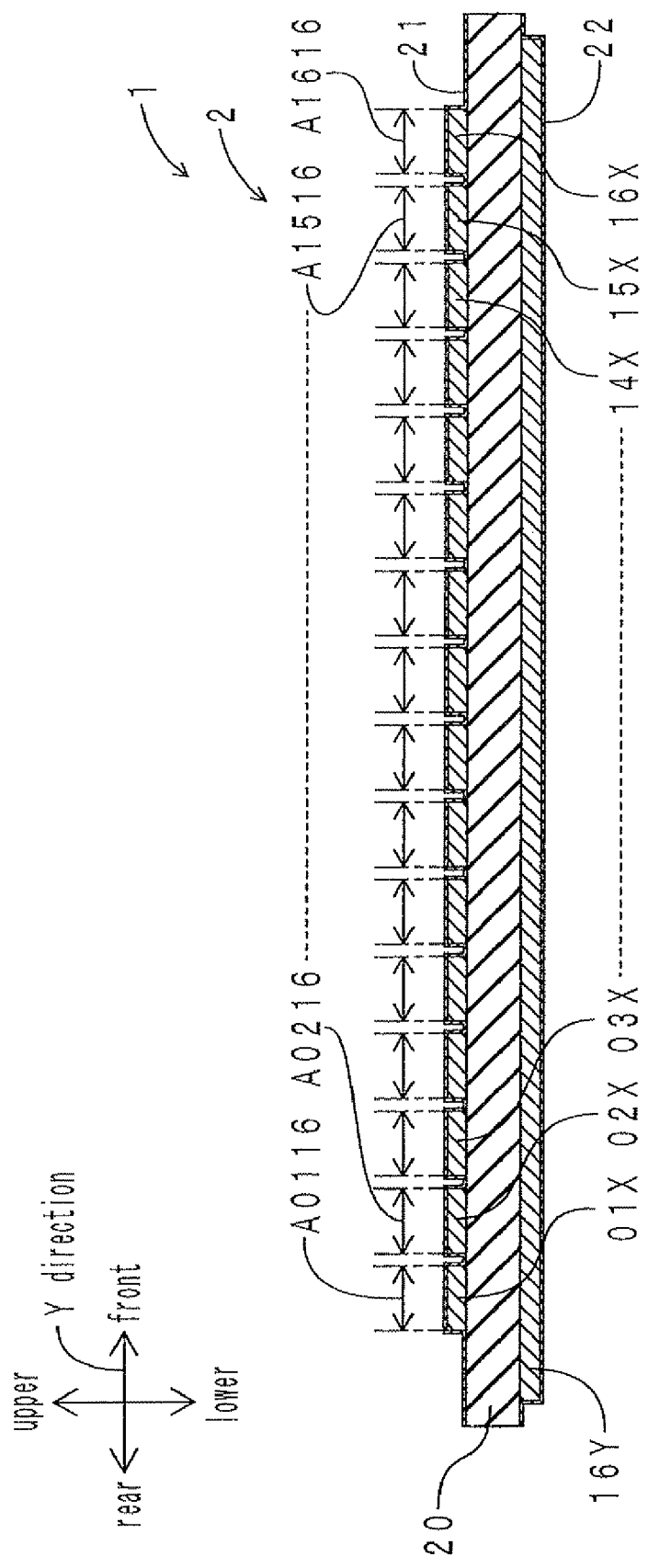
FIG. 7 is a sectional view taken along the line VII-VII of FIG. 6.

First, the constitution of a capacitive sensor according to this embodiment will be described. FIG. 6 is a perspective top view of the capacitive sensor according to this embodiment. Note that in FIG. 6, a surface side insulating cover layer and a back side insulating cover layer have been omitted. Further, a back side electrode and a back side conductor are indicated by thin lines, and detection portions are shown as the hatched portions. FIG. 7 is a sectional view taken along the line VII-VII of FIG. 6. Note that in FIG. 7, the thickness of a sensor main body in an up-down direction is emphasized. As shown in FIGS. 6 and 7, a capacitive sensor 1 according to this embodiment includes a sensor main body 2 and a calculation portion 3.

The sensor main body 2 includes a dielectric layer 20, surface side electrodes 01X to 16X, back side electrodes 01Y to 16Y, detection portions A0101 to A1616, surface side conductors 01x to 16x, back side conductors 01y to 16y, a surface side insulating cover layer 21, a back side insulating cover layer 22, a connector for surface side conductor 23, and a connector for back side conductor 24. Note that in the reference symbols "A00XX" denoting the detection portions, the first two digits "00" correspond to the surface side electrodes 01X to 16X, and the latter two digits "XX" correspond to the back side electrodes 01Y to 16Y.

The dielectric layer 20 is made of ether-based urethane rubber, and takes a sheet form. A hardness (type A durometer hardness: JIS K6253 (2006)) of the dielectric layer 20 is 90 degrees. The dielectric layer 20 extends in an X direction and a Y direction (a front-rear direction and a left-right direction).

A total of 16 surface side electrodes 01X to 16X are arranged on an upper surface of the dielectric layer 20. The surface side electrodes 01X to 16X are each formed to include acryl rubber and conductive carbon black. The surface side electrodes 01X to 16X each take a belt shape. The surface side electrodes 01X to 16X respectively extend in the X direction (left-right direction). The surface side electrodes 01X to 16X are arranged away from each other at predetermined intervals in the Y direction (front-rear direction) so as to be substantially parallel to each other. Surface side connection portions 01X1 to 16X1 are arranged on the respective left ends of the surface side electrodes 01X to 16X.

A total of 16 surface side conductors 01x to 16x are arranged on the upper surface of the dielectric layer 20. The surface side conductors 01x to 16x are each formed to include urethane rubber and silver powder. The surface side conductors 01x to 16x each take a linear shape. The connector for surface side conductor 23 is arranged at a left rear corner of the dielectric layer 20. The surface side conductors 01x to 16x are respectively connected to the surface side connection portions 01X1 to 16X1 and the connector for surface side conductor 23.

The surface side insulating cover layer 21 is arranged on top of the dielectric layer 20. The surface side insulating cover layer 21 is formed to include acrylic rubber. The surface side insulating cover layer 21 takes a sheet form. The surface side insulating cover layer 21 covers the dielectric layer 20, the surface side electrodes 01X to 16X, and the surface side conductors 01x to 16x from above.

A total of 16 back side electrodes 01Y to 16Y are arranged on a lower surface of the dielectric layer 20. The back side electrodes 01Y to 16Y are each formed to include acrylic rubber and conductive carbon black. The back side electrodes 01Y to 16Y each take a belt shape. The back side electrodes 01Y to 16Y each extend in the Y direction. The back side electrodes 01Y to 16Y are arranged away from each other at predetermined intervals in the X direction so as to be substantially parallel to each other. Back side connection portions 01Y1 to 16Y1 are arranged on the respective front ends of the back side electrodes 01Y to 16Y.

A total of 16 back side conductors 01y to 16y are arranged on the lower surface of the dielectric layer 20. The back side conductors 01y to 16y are each formed to include urethane rubber and silver powder. The back side conductors 01y to 16y each take a linear shape. The connector for back side conductor 24 is arranged at a left front corner of the dielectric layer 20. The back side conductors 01y to 16y are respectively connected to the back side connection portions 01Y1 to 16Y1 and the connector for back side conductor 24.

The back side insulating cover layer 22 is arranged on the back side of the dielectric layer 20. The back side insulating cover layer 22 is formed to include acrylic rubber. The back side insulating cover layer 22 takes a sheet form. The back side insulating cover layer 22 covers the dielectric layer 20, the back side electrodes 01Y to 16Y, and the back side conductors 01y to 16y from below.

As shown by the hatching in FIG. 6, the detection portions A0101 to A1616 are arranged in portions (overlapping portions) in which the surface side electrodes 01X to 16X and the back side electrodes 01Y to 16Y intersect in the up-down direction. A total of 256 (=16'16) detection portions A0101 to A1616 are arranged. The detection portions A0101 to A1616 are arranged at substantially equal intervals over substantially the entire surface of the sensor main body 2. Each detection portion A0101 to A1616 partially includes the surface side electrode 01X to 16X, the back side electrode 01Y to 16Y, and the dielectric layer 20.

The calculation portion 3 includes a power supply circuit 30, a Central Processing Unit (CPU) 31, a Random Access Memory (RAM) 32, a Read Only Memory (ROM) 33, and a display 34. The calculation portion 3 is electrically connected to the connector for surface side conductor 23 and the connector for back side conductor 24.

The power supply circuit 30 applies a sine wave-shaped alternating current voltage to the detection portions A0101 to A1616. A map indicating correspondence between electrostatic capacity and surface pressure in the detection portions A0101 to A1616 is stored in advance in the ROM 33. The ROM 33 also stores the following Equations (3) and (5). Impedance values and phase values input from the connector for surface side conductor 23 and the connector for back side conductor 24 are stored temporarily in the RAM 32. The CPU 31 extracts the electrostatic capacity of the detection portions A0101 to A1616 on the basis of the impedance and the phase values stored in the RAM 32 using Equations (3) and (5), as will be described below. The CPU 31 then calculates a surface pressure distribution of the sensor main body 2 from the electrostatic capacity. The display 34 displays the surface pressure distribution calculated by the CPU 31 on a screen (not shown), in the form of a three-dimensional graph, for example.

[Manufacturing Method]

Next, a manufacturing method for the capacitive sensor 1 according to this embodiment will be described. The manufacturing method for the capacitive sensor 1 according to this embodiment includes a coating preparation step, a surface side electrode printing step, a surface side conductor printing step, a surface side insulating cover layer printing step, a back side electrode printing step, a back side conductor printing step, and a back side insulating cover layer printing step.

In the coating preparation step, an electrode coating, a conductor coating, and a cover layer coating are respectively prepared. The electrode coating is prepared using the following procedure. First, 100 parts by mass of a polymer (acrylic rubber, product name Nipol (registered trademark) AR51, manufactured by Zeon Corporation), 1.00 parts by mass of a vulcanization aid (stearic acid, product name Lunac (registered trademark) S30, manufactured by Kao Corporation), 2.50 parts by mass of a vulcanizing accelerator (zinc dimethyldithiocarbamate, product name Nocceler (registered trademark) PZ, manufactured by Ouchi Shinko Chemical Industrial Co., Ltd.), and 0.50 parts by mass of a vulcanizing accelerator (ferric dimethyldithiocarbamate, product name Nocceler TTFE, manufactured by Ouchi Shinko Chemical Industrial Co., Ltd.) are weighed and then roll-milled. Thus, a rubber compound is prepared. Next, the prepared rubber compound is submerged in 1500 parts by mass of an organic solvent (methyl ethyl ketone, manufactured by Sankyo Chemical Co., Ltd.), whereupon the organic solvent is stirred to obtain a solution in which the rubber compound is dissolved evenly in the organic solvent. Next, 22.86 parts by mass of conductive carbon black (ketjen black, product name EC300J, manufactured by Lion Corporation) is added to the solution. Thus, a MEK (methyl ethyl ketone) solution having a solid ratio of approximately 7.8% by mass is obtained. Milling processing is then performed on the MEK solution to improve the dispersibility of the conductive carbon black in the MEK solution. More specifically, the MEK solution is introduced into a dyno-mill that rotates at 3200 rpm, and the MEK solution is circulated approximately 40 times. Next, 686.7 parts by mass of a printing solvent (diethylene glycol monobutyl ether acetate, manufactured by Sankyo Chemical Co., Ltd.) is added to the milled MEK solution. The MEK solution containing the added printing solvent is then moved to a container having a wide opening to increase the surface area of the MEK solution that is exposed to the atmosphere. The MEK solution is then left for approximately one day and stirred occasionally such that the MEK, which has a low boiling point, is sufficiently evaporated. Thus, the electrode coating is prepared. Note that the boiling point of the printing solvent is at least 200° C., and therefore volatilization of the printing solvent is negligible.

The conductor coating is prepared using the following procedure. First, 333 parts by mass of a polymer (obtained by dissolving polyurethane in MEK/toluene/isopropyl alcohol; product name Nippolan (registered trademark) 5230, manufactured by Nippon Polyurethane Industry Co., Ltd.) (the solid content of the polymer is 30% by mass, and therefore 333 parts by mass of the polymer corresponds to 100 parts by mass of polyurethane), 400 parts by mass of 10 μm flaked silver powder (product name FA-D-4, manufactured by DOWA Electronics Materials Co., Ltd.), 400 parts by mass of spherical silver powder at 1 μm (product name AG2-1C, manufactured by DOWA Electronics Materials Co., Ltd.), and 150 parts by mass of a printing solvent (butyl carbitol, manufactured by Sankyo Chemical Co., Ltd.) are weighed and stirred until evenly mixed. The stirred solution is then moved to a container having a wide opening to increase the surface area of the solution that is exposed to the atmosphere. The solution is then left for approximately one day and stirred occasionally such that the MEK, the toluene, and the isopropyl alcohol, which have low boiling points, are sufficiently evaporated. Thus, the conductor coating is prepared.

The cover layer coating is prepared using the following procedure. First, 100 parts by mass of a polymer (acrylic rubber, product name Nipol AR51, manufactured by Zeon Corporation), 1.00 parts by mass of a vulcanization aid (stearic acid, product name Lunac S30, manufactured by Kao Corporation), 2.50 parts by mass of a vulcanizing accelerator (zinc dimethyldithiocarbamate, product name Nocceler PZ, manufactured by Ouchi Shinko Chemical Industrial Co., Ltd.), and 0.50 parts by mass of a vulcanizing accelerator (ferric dimethyldithiocarbamate, product name Nocceler TTFE, manufactured by Ouchi Shinko Chemical Industrial Co., Ltd.) are weighed and then roll-milled. Thus, a rubber compound is prepared. Next, the prepared rubber compound is submerged in 300 parts by mass of a printing solvent (ethylene glycol monobutyl ether acetate, manufactured by Daicel Chemical Industries Ltd.) and stirred until evenly mixed. Thus, the cover layer coating is prepared.

Figure 8:
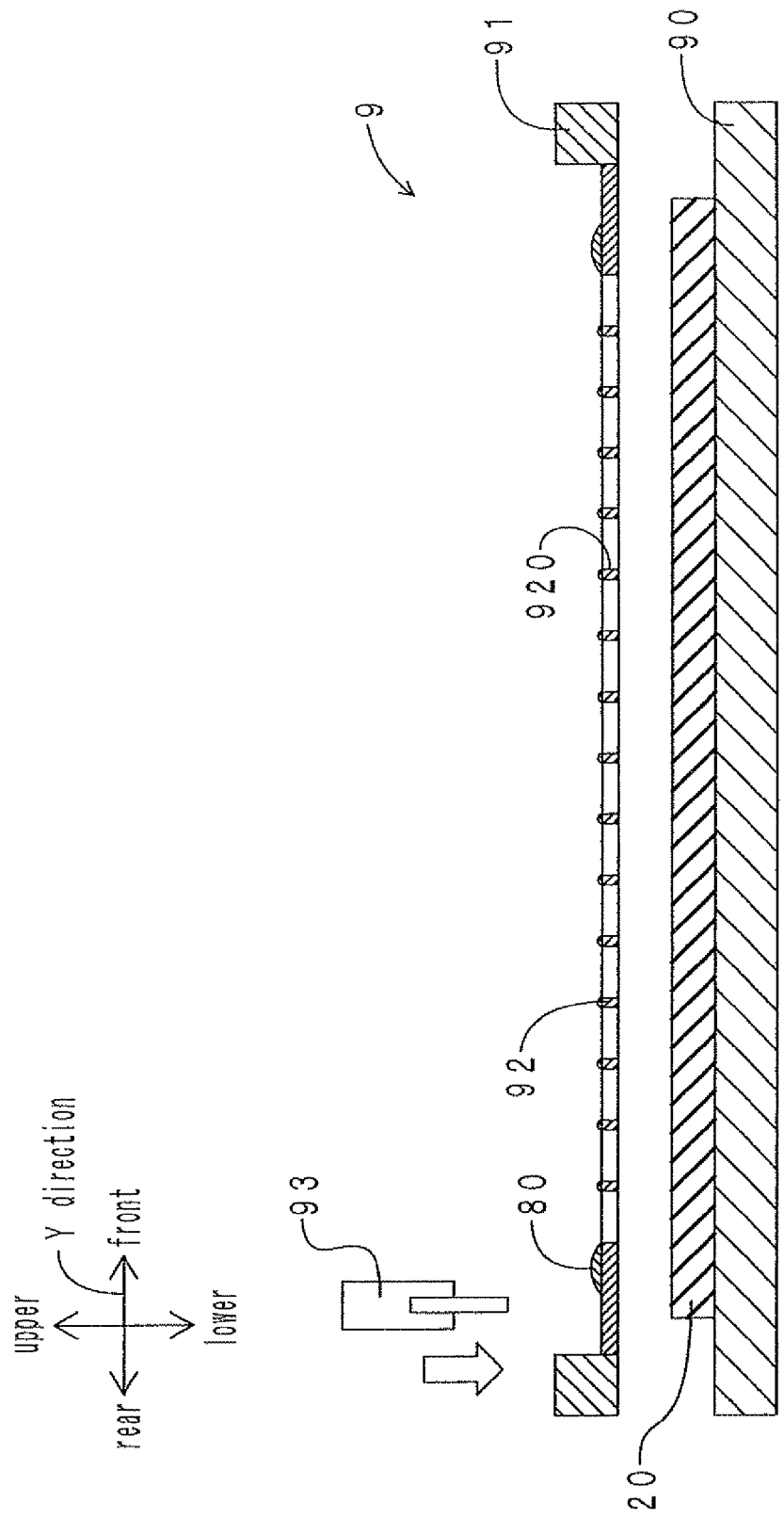
FIG. 8 is a pattern diagram showing the first half of a surface side electrode printing step in a manufacturing method for the capacitive sensor.
Figure 9:
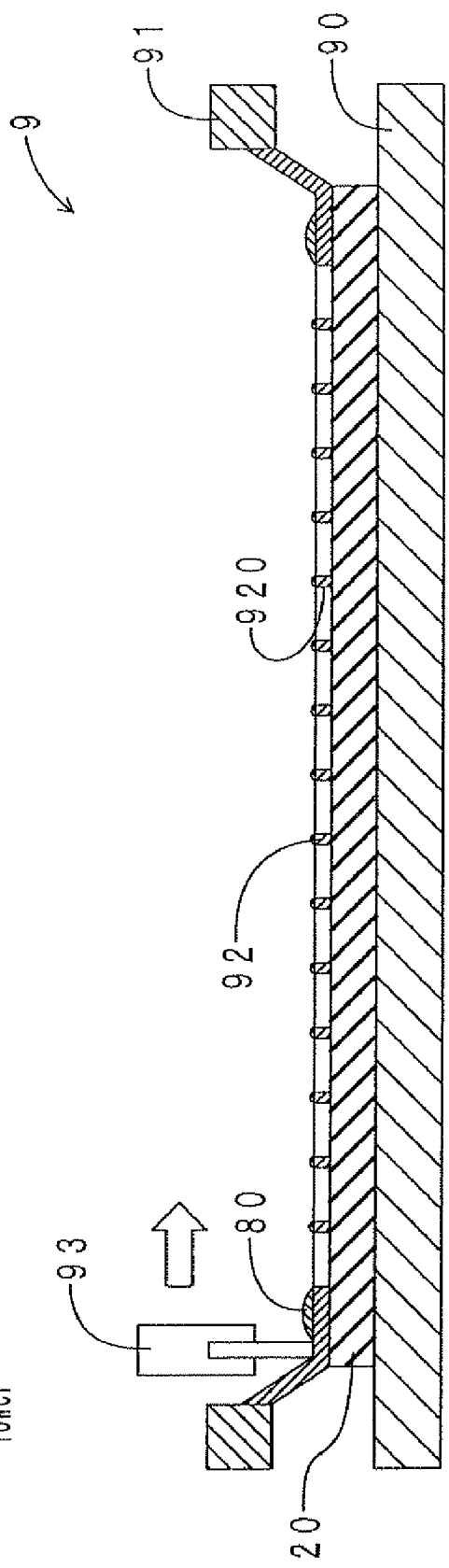
FIG. 9 is a pattern diagram showing the latter half of the same step.

In the surface side electrode printing step, the electrode coating prepared in the coating preparation step is printed onto the upper surface of the dielectric layer 20. FIG. 8 is a pattern diagram showing the first half of the surface side electrode printing step in the manufacturing method for the capacitive sensor according to this embodiment. FIG. 9 is a pattern diagram showing the latter half of the step.

As shown in FIGS. 8 and 9, in this step, an electrode coating 80 is printed onto the upper surface of the dielectric layer 20 using a screen printer 9. The screen printer 9 includes a table 90, a frame 91, a screen mask 92, and a squeegee 93. The dielectric layer 20 is placed on the table 90. The screen mask 92 is arranged above the table 90. The screen mask 92 is stretched over the frame 91. Holes 920 are opened in the screen mask 92 in accordance with the surface side electrodes 01X to 16X (see FIG. 7). The squeegee 93 is arranged above the screen mask 92.

In this step, first, the electrode coating 80 is placed onto the upper surface of the screen mask 92. Next, the lower surface of the screen mask 92 is pressed against the upper surface of the dielectric layer 20. Next, the squeegee 93 is moved in the Y direction such that the electrode coating 80 on the upper surface of the screen mask 92 is pressed into the holes 920. Thus, the surface side electrodes 01X to 16X (see FIG. 7) are printed onto sites on the upper surface of the dielectric layer 20 corresponding to the holes 920. The surface side electrodes 01X to 16X are then heated to vulcanize the polymer.

In the surface side conductor printing step, similarly to the surface side electrode printing step, the screen printer 9 is used to print the conductor coating prepared in the coating preparation step onto the upper surface of the dielectric layer 20. Thus, the surface side conductors 01*x* to 16*x* (see FIG. 6) are arranged on the upper surface of the dielectric layer 20. The surface side conductors 01*x* to 16*x* are then dried. Note that the holes 920 in the screen mask 92 are arranged in accordance with the surface side conductors 01*x* to 16*x*.

In the surface side insulating cover layer printing step, similarly to the surface side electrode printing step, the screen printer 9 is used to print the cover layer coating prepared in the coating preparation step onto the upper surfaces of the dielectric layer 20, the surface side electrodes 01X to 16X, and the surface side conductors 01*x* to 16*x*. Thus, the surface side insulating cover layer 21 (see FIG. 7) is arranged on the upper surfaces of the dielectric layer 20, the surface side electrodes 01X to 16X, and the surface side conductors 01*x* to 16*x*. The surface side insulating cover layer 21 is then heated to vulcanize the polymer. Note that the holes 920 in the screen mask 92 are arranged in accordance with the surface side insulating cover layer 21.

In the back side electrode printing step, similarly to the surface side electrode printing step, the screen printer 9 is used to print the electrode coating 80 prepared in the coating preparation step onto the lower surface (the lower surface in FIG. 7; during printing, this surface is oriented upward) of the dielectric layer 20. Thus, the back side electrodes 01Y to 16Y (see FIG. 6) are arranged on the lower surface of the dielectric layer 20. The back side electrodes 01Y to 16Y are then heated to vulcanize the polymer.

In the back side conductor printing step, similarly to the surface side conductor printing step, the screen printer 9 is used to print the conductor coating prepared in the coating preparation step onto the lower surface of the dielectric layer 20. Thus, the back side conductors 01*y* to 16*y* (see FIG. 6) are arranged on the lower surface of the dielectric layer 20. The back side conductors 01*y* to 16*y* are then dried.

In the back side insulating cover layer printing step, similarly to the surface side insulating cover layer printing step, the screen printer 9 is used to print the cover layer coating prepared in the coating preparation step onto the lower surfaces of the dielectric layer 20, the back side electrodes 01Y to 16Y, and the back side conductors 01*y* to 16*y*. Thus, the back side insulating cover layer 22 (see FIG. 7) is arranged on the lower surfaces of the dielectric layer 20, the back side electrodes 01Y to 16Y, and the back side conductors 01*y* to 16*y*. The back side insulating cover layer 22 is then heated to vulcanize the polymer. Thus, the capacitive sensor 1 according to this embodiment is manufactured.

[Operation]

Next, an operation of the capacitive sensor 1 according to this embodiment will be described. First, an electrostatic capacity calculation method employed by the calculation portion 3 will be described. This electrostatic capacity calculation method is executed in relation to each of the detection portions A1010 to A1616.

As shown above in Equation (2), the electric resistance of an object is proportionate to its length. Conductivity of the surface side electrodes 01X to 16X and the back side electrodes 01Y to 16Y is secured by the conductive carbon black. Therefore, the electric resistance of the surface side electrodes 01X to 16X and the back side electrodes 01Y to 16Y is larger than that of the surface side conductors 01*x* to 16*x* and the back side conductors 01*y* to 16*y*.

Further, a distance (corresponding to the length L in Equation (2)) from each of the surface side connection portions 01X1 to 16X1 to the detection portions A0101 to A1616 in the surface side electrodes 01X to 16X is not constant. In other words, the electric resistance of the surface side electrodes 01X to 16X from the surface side connection portions 01X1 to 16X1 to the detection portions A0101 to A1616 is not constant. Focusing on the surface side electrode 01X in FIG. 6, for example, the distance from the surface side connection portion 01X1 to the detection portion A0116 is greater than the distance from the surface side connection portion 01X1 to the detection portion A0101. Accordingly, the electric resistance from the surface side connection portion 01X1 to the detection portion A0116 is greater than the electric resistance from the surface side connection portion 01X1 to the detection portion A0101. Similarly, the electric resistance of the back side electrodes 01Y to 16Y from the back side connection portions 01Y1 to 16Y1 to the detection portions A0101 to A1616 is not constant.

Figure 10:
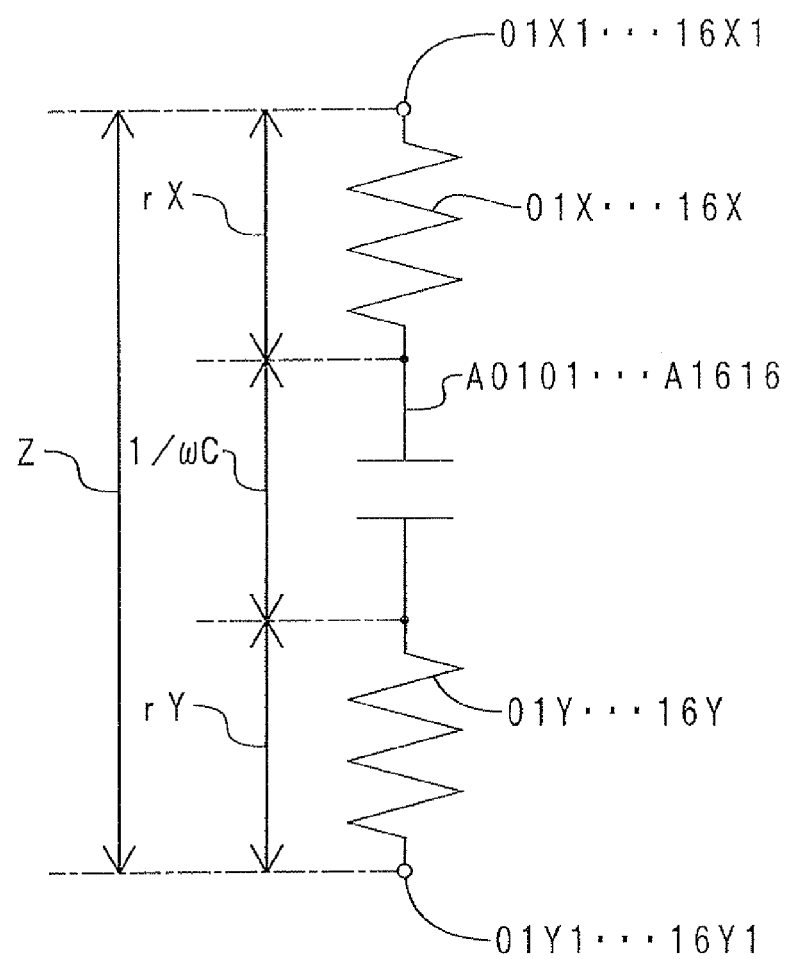
FIG. 10 is an equivalent circuit diagram of a given surface side electrode-detection portion-back side electrode of the capacitive sensor.

FIG. 10 is an equivalent circuit diagram showing a given surface side electrode-detection portion-back side electrode of the capacitive sensor according to this embodiment. As shown in FIG. 10, a given surface side electrode 01X to 16X-detection portion A0101 to A1616-back side electrode 01Y to 16Y is equivalent to an RC series circuit. In other words, an impedance Z of the given surface side electrode 01X to 16X-detection portion A0101 to A1616-back side electrode 01Y to 16Y is constituted by an electric resistance rX of the surface side electrode 01X to 16X from the surface side connection portion 01X1 to 16X1 to the detection portion A0101 to A1616, a capacitive reactance $1/\omega C$ of the detection portion A0101 to A1616, and an electric resistance rY of the back side electrode 01Y to 16Y from the back side connection portion 01Y1 to 16Y1 to the detection portion A0101 to A1616.

Meanwhile, the impedance Z of the given surface side electrode 01X to 16X-detection portion A0101 to A1616-back side electrode 01Y to 16Y and a displacement angle (phase) θ of a current relative to a voltage (see FIG. 11 to be described below) are input into the calculation portion 3 from the sensor main body 2.

Figure 11:
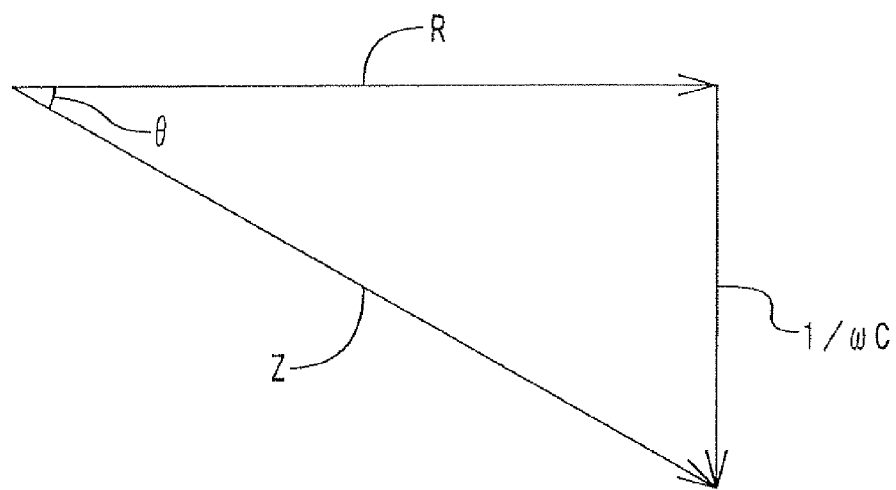
FIG. 11 is a view showing an impedance vector diagram of the RC series circuit.

In the calculation portion 3, the effect of the electric resistances rX, rY must be separated from the impedance Z to calculate an electrostatic capacity C of the detection portions A0101 to A1616 with a high degree of precision. FIG. 11 is a view showing an impedance vector diagram of the RC series circuit. Further, Equations (3) to (5) show impedance relations of the RC series circuit.

$$\cos \theta = R/Z \qquad (3)$$

$$\sin \theta = (1/\omega C)/Z \qquad (4)$$

$$Z = \sqrt{(R^2 + (1/\omega C)^2)} \qquad (5)$$

Here, an electric resistance R is the sum of the electric resistance rX and the electric resistance rY. Further, ω denotes the angular frequency. Note that the angular frequency ω is a known item.

Equation (3) and Equation (5) are stored in the ROM 33 in advance. The CPU substitutes the impedance Z and the phase θ, which are stored temporarily in the RAM 32, into Equation (3) to calculate the electric resistance R. The impedance Z7, the electric resistance R, and the angular frequency ω are then substituted into Equation (5) to calculate the electrostatic capacity C.

Next, an operation of the capacitive sensor during measurement of a measurement subject will be described. First, before the measurement subject is placed on the sensor main body 2, the electrostatic capacity calculation method described above is used to calculate the electrostatic capacity C in each of the detection portions A0101 to A1616. In other words, the electrostatic capacity C is calculated in a scan-like manner from the detection portion A0101 to the detection portion A1616. The calculated electrostatic capacity C is stored in the RAM 32 in relation to each of the detection portions A0101 to A1616.

Next, the measurement subject is placed on the sensor main body 2, whereupon the electrostatic capacity C is calculated in relation to each of the detection portions A0101 to A1616 using the electrostatic capacity calculation method described above in a similar manner to the calculation performed prior to placement of the measurement subject. In other words, the electrostatic capacity C is calculated in a scan-like manner from the detection portion A0101 to the detection portion A1616. The calculated electrostatic capacity C is stored in the RAM 32 in relation to each of the detection portions A0101 to A1616.

The CPU 31 then calculates the surface pressure applied to the sensor main body 2 from a variation ΔC in the electrostatic capacity C before and after placement of the measurement subject. More specifically, a map indicating correspondence between the electrostatic capacity C and the surface pressure is stored in the ROM 33 in advance. The surface pressure of a given detection portion A0101 to A1616 is then calculated by substituting the electrostatic capacity C into the map. The surface pressure is then displayed on the screen of the display 34 in relation to each of the detection portions A0101 to A1616.

Then, by integrating the variation ΔC in the electrostatic capacity C of each of the detection portions A0101 to A1616, a total load applied to all of the detection portions A0101 to A1616, or in other words, to the sensor main body 2, can be displayed on the screen of the display 34.

[Advantageous Effects]

Next, advantageous effects of the capacitive sensor 1 according to this embodiment will be described. According to the capacitive sensor 1 of this embodiment, the dielectric layer 20 is made of ether-based urethane rubber. Hence, in comparison with a case in which the dielectric layer 20 is constituted by air, the electrostatic capacity C output by the detection portions A0101 to A1616 increases. Further, the variation ΔC in the electrostatic capacity C increases.

Further, the surface side electrodes 01X to 16X and the back side electrodes 01Y to 16Y both take a belt shape. Moreover, the detection portions A0101 to A1616 are arranged using the intersecting portions between the surface side electrodes 01X to 16X and the back side electrodes 01Y to 16Y. Hence, the number of arranged electrodes is reduced. The number of arranged conductors is also reduced. More specifically, a total of 256 detection portions A0101 to A1616 are arranged on the sensor main body 2. When an electrode is arranged for each detection portion A0101 to A1616, 256 surface side electrodes and 256 back side electrodes are required. According to the capacitive sensor 1 of this embodiment, on the other hand, a total of only 32 (=16+16) surface side electrodes 01X to 16X and back side electrodes 01Y to 16Y need be provided to secure the 256 detection portions A0101 to A1616, and therefore the number of arranged electrodes is reduced.

Further, the surface side electrodes 01X to 16X and the back side electrodes 01Y to 16Y are formed to include acrylic rubber and conductive carbon black. Hence, when a load is applied by the measurement subject, the surface side electrodes 01X to 16X and the back side electrodes 01Y to 16Y are both expandable and contractible together with the dielectric layer 20 in accordance with the load. Therefore, expansion and contraction of the dielectric layer 20 is unlikely to be restricted by the surface side electrodes 01X to 16X or the back side electrodes 01Y to 16Y.

Further, the surface side conductors 01x to 16x and the back side conductors 01y to 16y are formed to include urethane rubber and silver powder. Hence, when a load is applied by the measurement subject, the surface side conductors 01x to 16x and the back side conductors 01y to 16y can expand and contract in accordance with the load. Therefore, expansion and contraction of the dielectric layer 20 is unlikely to be restricted by the surface side conductors 01x to 16x or the back side conductors 01y to 16y.

Further, according to the capacitive sensor 1 of this embodiment, the electric resistance rX from the surface side connection portions 01X1 to 16X1 to the detection portions A0101 to A1616 and the electric resistance rY from the back side connection portions 01Y1 to 16Y1 to the detection portions A0101 to A1616 are separated from the impedance Z. In other words, the electrostatic capacity C of the detection portions A0101 to A1616 is extracted from the impedance Z. Therefore, the measurement precision of the surface pressure distribution is high.

Further, according to the capacitive sensor 1 of this embodiment, the calculation portion 3 can calculate the total load applied to the sensor main body 2 by integrating the variation ΔC in the electrostatic capacity C of the detection portions A0101 to A1616. Hence, the weight of the measurement subject can be detected.

Further, according to the capacitive sensor 1 of this embodiment, the surface side electrodes 01X to 16X are arranged at substantially equal intervals in the X direction and the Y direction over the entire surface of the sensor main body 2. Similarly, the back side electrodes 01Y to 16Y are arranged at substantially equal intervals in the X direction and the Y direction over the entire surface of the sensor main body 2. Furthermore, the surface side electrodes 01X to 16X and the back side electrodes 01Y to 16Y are arranged to be substantially orthogonal to each other when seen from the up-down direction. Hence, the detection portions A0101 to A1616 can be dispersed over the entire surface of the sensor main body 2. As a result, of the entire surface of the sensor main body 2, the surface area of portions in which the surface pressure is detected can be increased.

Further, according to the capacitive sensor 1 of this embodiment, the surface side electrodes 01X to 16X, the surface side conductors 01x to 16x, the back side electrodes 01Y to 16Y, and the back side conductors 01y to 16y are arranged on the dielectric layer 20 using a screen printing method. Therefore, the constitutional elements required for surface pressure measurement can be integrated in a comparatively simple manner. As a result, the production efficiency of the sensor main body 2, and therefore the capacitive sensor 1, is high.

Furthermore, the surface side electrodes 01X to 16X and the back side electrodes 01Y to 16Y are printed directly onto the dielectric layer 20. Therefore, positioning of the surface side electrodes 01X to 16X and the back side electrodes 01Y to 16Y is easy. Hence, the detection portions A0101 to A1616 can be arranged accurately in desired positions.

Furthermore, the capacitive sensor 1 according to this embodiment is provided with the surface side insulating cover layer 21 and the back side insulating cover layer 22. Hence, conduction from the surface side electrodes 01X to 16X and the surface side conductors 01x to 16x to a member outside the capacitive sensor 1 can be suppressed. Likewise, conduction from the back side electrodes 01Y to 16Y and the back side conductors 01y to 16y to a member outside the capacitive sensor 1 can be suppressed.

Further, the blended amount (critical volume fraction: φc) of conductive carbon black at a first polarity change point, at which the electric resistance decreases to cause a transition between insulator and conductor in a percolation curve expressing a relationship between the electric resistance and the blended amount of conductive carbon black in the elastomer composition forming the surface side electrodes 01X to 16X and the back side electrodes 01Y to 16Y of the capacitive sensor 1 according to this embodiment is approximately 4 vol %. Therefore, the conductive carbon black forms an aggregate easily. Hence, the surface side electrodes 01X to 16X and the back side electrodes 01Y to 16Y having favorable conductivity can be obtained with a comparatively small amount of conductive carbon black.

Fourth Embodiment

A capacitive sensor according to this embodiment differs from the capacitive sensor according to the third embodiment by the constitution in which the sensor main body is provided with an insulating tube member. Therefore, only this difference will be described.

Figure 12:
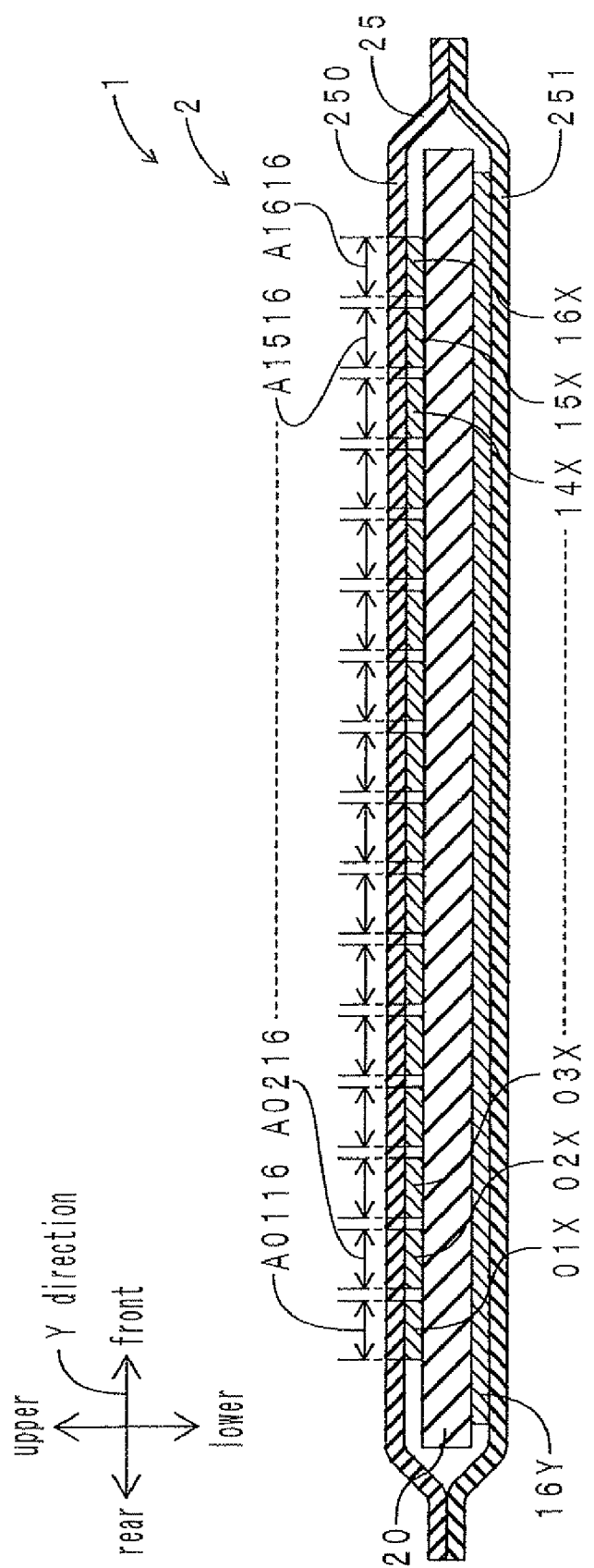
FIG. 12 is a sectional view of a capacitive sensor according to a fourth embodiment of the present invention, taken in a Y direction.

FIG. 12 is a sectional view of the capacitive sensor according to this embodiment, taken in the Y direction. Note that portions corresponding to FIG. 7 are denoted by identical reference symbols with those in FIG. 7. As shown in FIG. 12, the sensor main body 2 includes an insulating tube member 25. The insulating tube member 25 includes a surface side insulating sheet 250 and a back side insulating sheet 251. The materials of the surface side insulating sheet 250 and the back side insulating sheet 251 are identical to the materials of the surface side insulating cover layer and the back side insulating cover layer according to the third embodiment.

A total of 16 surface side electrodes 01X to 16X are printed onto an inner surface of the surface side insulating sheet 250. A total of 16 back side electrodes 16Y are printed onto an inner surface of the back side insulating sheet 251. The dielectric layer 20 is interposed between the surface side electrodes 01X to 16X and the back side electrodes 16Y inside the insulating tube member 25.

A manufacturing method for the capacitive sensor according to this embodiment includes a coating preparation step, a surface side electrode printing step, a surface side conductor printing step, a back side electrode printing step, a back side conductor printing step, an insulating tube member manufacturing step, and a dielectric layer insertion step. In the coating preparation step, the electrode coating and the conductor coating are respectively prepared. In the surface side electrode printing step, the surface side electrodes 01X to 16X are printed onto the inner surface of the surface side insulating sheet 250 using a screen printer. The surface side electrodes 01X to 16X are then vulcanized. In the surface side conductor printing step, the surface side conductors are printed onto the inner surface of the surface side insulating sheet 250 using a screen printer. The surface side conductors are then dried. In the back side electrode printing step, the back side electrodes 16Y are printed onto the inner surface of the back side insulating sheet 251 using a screen printer. The back side electrodes 16Y are then vulcanized. In the back side conductor printing step, the back side conductors are printed onto the inner surface of the back side insulating sheet 251 using a screen printer. The back side conductors are then dried. In the insulating tube member manufacturing step, the surface side insulating sheet 250 and the back side insulating sheet 251 are adhered to each other. Thus, the insulating tube member 25 is manufactured. In the dielectric layer insertion step, the dielectric layer 20 is inserted into the interior of the insulating tube member 25.

With respect to portions having common constitutions, the capacitive sensor 1 according to this embodiment exhibits similar advantageous effects to the capacitive sensor of the third embodiment.

Further, according to the capacitive sensor 1 of this embodiment, printing is not performed directly onto the dielectric layer 20. Therefore, a material that is not suitable for printing (such as a foam body, for example) can be used as the dielectric layer 20. Hence, the freedom of material selection of the dielectric layer 20 is improved.

Further, according to the capacitive sensor 1 of this embodiment, the constitutional elements required for surface pressure measurement, namely the dielectric layer 20, the surface side electrodes 01X to 16X, the surface side conductors, the back side electrodes 16Y, and the back side conductors, are accommodated inside the insulating tube member 25. Hence, conduction between these members and a member outside the insulating tube member 25 can be suppressed.

Other Embodiments

Embodiments of the second capacitive sensor according to the present invention are described above. However, the embodiments are not limited to the above embodiments, and various modified and improved embodiments may be implemented by a person skilled in the art.

For example, in the above embodiments, the electrostatic capacity C before the measurement subject is placed and the electrostatic capacity C after the measurement subject is placed are calculated, whereupon the surface pressure distribution is determined from the variation $\Delta C$ in the electrostatic capacity. However, a surface pressure before the placement may be determined from the electrostatic capacity C before the placement of the measurement subject, a surface pressure after the placement may be determined from the electrostatic capacity C after the placement of the measurement subject, and the surface pressure distribution may be determined from variation in the surface pressure.

Further, there are no particular limitations on the numbers and the intersection angles of the surface side electrodes 01X to 16X and the back side electrodes 01Y to 16Y. There are also no particular limitations on the interval between adjacent surface side electrodes 01X to 16X and the interval between adjacent back side electrodes 01Y to 16Y Furthermore, an antioxidant may be printed to cover the surface side conductors $01x$ to $16x$ and the back side conductors $01y$ to $16y$. In so doing, oxidation of the silver contained in the conductors can be suppressed. Further, there are no particular limitations on the application of the capacitive sensor 1. For example, the capacitive sensor 1 may be used as a seating position detection sensor for a vehicle seat, a touch sensor, a user position detection sensor or the like in an electric carpet, and so on. The sensor main body 2 of the capacitive sensor 1 contains an elastomer, and is therefore particularly flexible. Hence, a user does not feel much discomfort even when the capacitive sensor 1 is arranged comparatively close to the body of the user. Accordingly, the capacitive sensor 1 is particularly suitable for detecting a load from a human being (bodyweight, for example). Further, a personal computer may be used as the calculation portion 3.

Further, the manufacturing method for the capacitive sensor 1 may be executed in order of the surface side conductor printing step to the surface side electrode printing step. Similarly, the manufacturing method may be executed in order of the back side conductor printing step to the back side electrode printing step.

Further, there are no particular limitations on the printing method employed in the manufacturing method for the capacitive sensor 1, and instead of screen printing, inkjet printing, flexographic printing, gravure printing, pad printing, lithography, and so on may be used.

Further, the elastomer constituting the dielectric layer 20 may be selected appropriately from rubber and thermoplastic elastomers. There are no particular limitations on the elastomer. For example, an elastomer having a large specific dielectric constant is preferable in terms of increasing the capacitance. For example, an elastomer having a specific dielectric constant at room temperature of 3 or more, and more preferably 5 or more, may be employed. An elastomer containing a polar functional group such as an ester group, a carboxyl group, a hydroxyl group, a halogen group, an amide group, a sulfone group, a urethane group, or a nitrile group, or an elastomer to which a polar low molecular weight compound containing these polar functional groups is added, for example, may be employed favorably. The elastomer may be crosslinked or not crosslinked. Further, by adjusting the Young's modulus of the elastomer, the detection sensitivity and the detection range can be adjusted in accordance with the application. In other words, the dielectric layer 20 may be selected from the dielectric layers 20 having various Young's moduli in accordance with the load of the measurement subject. In particular, when the load of the measurement subject is small, a foam body is used favorably as the elastomer of the dielectric layer 20. This is because the Young's modulus of a foam body is small, and therefore the dielectric layer 20 deforms sufficiently even when the load of the measurement subject is small. In other words, this is because the surface pressure and the load of the measurement subject can be detected reliably.

Examples of preferred elastomers include silicone rubber, acrylonitrile-butadiene copolymer rubber, acrylic rubber, epichlorohydrin rubber, chlorosulfonated polyethylene, chlorinated polyethylene, and urethane rubber.

There are no particular limitations on the thickness of the dielectric layer. For example, the thickness of the dielectric layer 20 is preferably set at 1 µm or more and 3000 µm or less from the viewpoints of reducing the size of the sensor main body 2 and improving the detection sensitivity by increasing the electrostatic capacity C in proportion to the inverse of the thickness of the dielectric layer 20 (i.e. the distance between electrodes d), as shown by Equation (1). A thickness of 50 µm or more and 500 µm or less is more preferable.

Further, the elastomer constituting the surface side electrodes 01X to 16X and the back side electrodes 01Y to 16Y may be the same as the elastomer used for the dielectric layer 20 or may be different. When the surface side electrodes 01X to 16X, the back side electrodes 01Y to 16Y and the dielectric layer 20 are constituted by the identical elastomer, the ability of the surface side electrodes 01X to 16X and the back side electrodes 01Y to 16Y to follow deformation of the dielectric layer 20 is improved. Furthermore, adhesiveness between the dielectric layer 20 and the surface side electrodes 01X to 16X and the back side electrodes 01Y to 16Y is improved, and therefore the surface side electrodes 01X to 16X and the back side electrodes 01Y to 16Y are less likely to peel away from the dielectric layer 20 despite cyclic fatigue, leading to an improvement in reliability.

Elastomers that are suitably used for the surface side electrodes 01X to 16X and the back side electrodes 01Y to 16Y include silicone rubber, ethylene-propylene copolymer rubber, natural rubber, styrene-butadiene copolymer rubber, acrylonitrile-butadiene copolymer rubber, acrylic rubber, epichlorohydrin rubber, chlorosulfonated polyethylene, chlorinated polyethylene, and urethane rubber.

Furthermore, there are no particular limitations on the shape of the conductive fillers blended into the elastomer in the surface side electrodes 01X to 16X and the back side electrodes 01Y to 16Y, and the conductive fillers may have a spherical shape, a needle shape, a square column shape, and so on. An aspect ratio (the ratio between the short side and the long side) of the conductive fillers is preferably 1 or more, for example. When needle-shaped conductive fillers having a comparatively large aspect ratio are used, for example, a three-dimensional conductive network can be formed easily, and therefore high conductivity can be realized with a small amount of the fillers. Moreover, conductivity variation during expansion and contraction of the surface side electrodes 01X to 16X and the back side electrodes 01Y to 16Y can be suppressed.

Further, average particle diameter, compatibility with the elastomer, and so on may be taken into consideration when selecting the conductive fillers. For example, when spherical conductive fillers are employed, the average particle diameter (primary particle) of the conductive fillers is preferably 0.01 µm or more and 0.5 µm or less. When the average particle diameter is smaller than 0.01 µm, the cohesiveness of the fillers is high, and therefore the fillers cannot easily be dispersed evenly when the electrode coating is prepared. Hence, the average particle diameter is preferably 0.03 µm or more. Conversely, when the average particle diameter exceeds 0.5 µm, it becomes difficult to form an aggregate (secondary particle). Hence, the average particle diameter is preferably 0.1 µm or less. Note that the critical volume fraction ($\phi c$) in a percolation curve can be adjusted within a desired range by appropriately adjusting the combination of the conductive fillers and the elastomer, the average particle diameter of the conductive fillers, and so on.

To realize a desired conductivity, the conductive fillers are preferably blended at a ratio of at least the critical volume fraction ($\phi c$) in a percolation curve. On the other hand, when the filling rate of the conductive fillers exceeds 30 vol %, blending with the elastomer becomes difficult, leading to a reduction in moldability and a reduction in the stretchability of the surface side electrodes 01X to 16X and the back side electrodes 01Y to 16Y. Hence, the filling rate of the conductive fillers is preferably 30 vol % or less. Further, to secure stretchability in the surface side electrodes 01X to 16X and the back side electrodes 01Y to 16Y, a comparatively small amount of the conductive fillers is preferably blended so as to realize high conductivity. Accordingly, the filling rate of the conductive fillers is preferably set at 25 vol % or less when the volume of the surface side electrodes 01X to 16X and the back side electrodes 01Y to 16Y is 10 vol %, and more preferably at 15 vol % or less.

There are also no particular limitations on the thickness of the surface side electrodes 01X to 16X and the back side electrodes 01Y to 16Y, but the thickness is preferably set at 1 µm or more and 100 µm or less, taking into consideration the ability of the surface side electrodes 01X to 16X and the back side electrodes 01Y to 16Y to follow the dielectric layer 20 and in order to reduce the size of the sensor main body 2. Further, Young's modulus of the surface side electrodes 01X to 16X and the back side electrodes 01Y to 16Y is preferably 0.1 MPa or more and 10 MPa or less to improve the ability of the surface side electrodes 01X to 16X and the back side electrodes 01Y to 16Y to follow deformation of the dielectric layer 20. Likewise, elongation at break in the tensile test (JIS K6251) is preferably 200% or more.

Further, the electric resistance of the surface side electrodes 01X to 16X and the back side electrodes 01Y to 16Y is preferably 100 kΩ or less and more preferably 10 kΩ or less in the thickness direction and the surface direction. Here, variation in the conductivity of the surface side electrodes 01X to 16X and the back side electrodes 01Y to 16Y remains small even during expansion and contraction. For example, when the surface side electrodes 01X to 16X and the back side electrodes 01Y to 16Y are elongated in one direction such that a distance between terminals is extended to 100%, if a resistance across terminals (R1) is 10 times or less a resistance across terminals before elongation ($R1/R0 \leq 10$), it can be said that "variation in the conductivity of the electrode remains small even during expansion and contraction", similarly to the first capacitive sensor according to the present invention as described above.

In addition to the elastomer and the conductive fillers described above, various additives may be blended in the surface side electrodes 01X to 16X and the back side electrodes 01Y to 16Y. Examples of these additives include a crosslinking agent, a vulcanizing accelerator, a vulcanizing aid, an age resistor, a plasticizer, a softener, and a colorant.

The elastomer constituting the surface side conductors $01x$ to $16x$ and the back side conductors $01y$ to $16y$ may be the same as the elastomer used for the dielectric layer 20, the surface side electrodes 01X to 16X, and the back side electrodes 01Y to 16Y or may be different. Suitable examples of the elastomer include silicone rubber, ethylene-propylene copolymer rubber, natural rubber, styrene-butadiene copolymer rubber, acrylonitrile-butadiene copolymer rubber, acrylic rubber, epichlorohydrin rubber, chlorosulfonated polyethylene, chlorinated polyethylene, and urethane rubber.

Further, there are no particular limitations on the type of conductive particles as long as the conductivity thereof is high. For example, metal powder made of silver, gold, copper, nickel, and so on may be employed. Further, to realize the desired conductivity, the filling rate of the conductive particles in the elastomer is preferably set at 20 vol % or more when the volume of the surface side conductors $01x$ to $16x$ and the back side conductors $01y$ to $16y$ is 100 vol %. The filling rate of the conductive particles in the elastomer is preferably 50 vol % or less so as to suppress reductions in the stretchability of the surface side conductors $01x$ to $16x$ and the back side conductors $01y$ to $16y$.

Further, a sheet made of acrylic rubber, urethane rubber, silicone rubber, ethylene-propylene copolymer rubber, natural rubber, styrene-butadiene rubber, acrylonitrile-butadiene rubber, epichlorohydrin rubber, chlorosulfonated polyethylene, chlorinated polyethylene, and so on may be used as the material for forming the surface side insulating cover layer 21, the back side insulating cover layer 22, and the insulating tube member 25.

EXAMPLES

Next, the present invention will be described in detail using examples.

(1) First, a test performed to measure capacitance variation relative to elongation deformation in the capacitive sensor 4 according to the first embodiment (see FIGS. 2 and 3) will be described.

(Test Method)

A manufacturing method for the capacitive sensor 4 will be described. First, the electrode coating, the conductor coating, and the cover film coating were respectively prepared.

[Electrode Coating]

First, 100 parts by mass of an acrylic rubber polymer ("Nipol AR51", manufactured by Zeon Corporation), 1 part by mass of stearic acid serving as vulcanization aid ("Lunac S30", manufactured by Kao Corporation), 2.5 parts by mass of zinc dimethyldithiocarbamate serving as vulcanizing accelerator "Nocceler PZ", manufactured by Ouchi Shinko Chemical Industrial Co., Ltd.), and 0.5 parts by mass of ferric dimethyldithiocarbamine ("Nocceler TTFE", manufactured by Ouchi Shinko Chemical Industrial Co., Ltd.) were mixed by a roll mill to prepare an elastomer composition. The prepared elastomer composition was then dissolved in 1500 parts by mass of methyl ethyl ketone (MEK). Next, 22.86 parts by mass of ketjen black serving as conductive fillers ("EC600JD", manufactured by Lion Corporation, average particle diameter 40 nm) was added to the solution so as to obtain a MEK solution having a solid concentration of approximately 7.8% by mass. The obtained MEK solution was then mixed in a dyno-mill to disperse the ketjen black. Next, 686.7 parts by mass of a diethylene glycol monobutyl ether acetate serving as printing solvent was added to the MEK solution. The solution was then moved to a container having a wide opening so as to increase contact with the atmosphere, and then left at room temperature for one day and stirred occasionally. Thus, the MEK, which has a low boiling point, was evaporated. Thus, the electrode coating was prepared.

[Conductor Coating]

First, 400 parts by mass of each of two types of silver powder ("FA-D-4" and "AG2-1C", manufactured by DOWA Electronics Materials Co., Ltd.) were added to 333 parts by mass of a solution obtained by dissolving an urethane polymer in a low boiling point solvent ("Nippolan 5230", manufactured by Nippon Polyurethane Industry Co., Ltd., solid concentration 30% by mass). Next, 150 parts by mass of butyl carbitol serving as printing solvent were added, whereupon the mixture was stirred. The solution was then moved to a container having a wide opening so as to increase contact with the atmosphere, whereupon the solution was left at room temperature for approximately one day and stirred occasionally such that the low boiling point solvent evaporated. Thus, the conductor coating was prepared.

[Cover Film Coating]

First, 100 parts by mass of an acrylic rubber polymer (same as above), 1 part by mass of stearic acid serving as vulcanization aid (same as above), 2.5 parts by mass of zinc dimethyldithiocarbamate serving as vulcanizing accelerator (same as above), and 0.5 parts by mass of ferric dimethyldithiocarbamine (same as above) were mixed by the roll mill to prepare an elastomer composition. The prepared elastomer composition was then dissolved in 300 parts by mass of an ethylene glycol monobutyl ether acetate serving as printing solvent to obtain a cover film coating.

Next, an ether-based urethane rubber sheet having a thickness of 300 μm (type A durometer hardness 90 degrees: JIS K6253 (2006)) was prepared as the dielectric layer. The coatings described above were respectively printed onto the surface and the back of the urethane rubber sheet in sequence. A table sliding semiautomatic printing machine ("SSA-PC660IP", manufactured by Tokai Seiki Co. Ltd.) was used for printing.

More specifically, first, a conductor plate and the urethane rubber sheet were set on the printing machine. The conductor coating was then placed on the conductor plate, whereupon a squeegee was moved on the plate in a scan-like manner to print a conductor on the surface of the urethane rubber sheet. The urethane rubber sheet was then left in a drying oven at approximately 140° C. for approximately 20 minutes in order to dry the urethane rubber sheet and advance the crosslinking reaction. Next, an electrode plate and the urethane rubber sheet on which the conductor was formed were set on the printing machine. The electrode coating was then placed on the plate, whereupon the squeegee was moved on the plate in a scan-like manner to print an electrode on the surface of the urethane rubber sheet. The urethane rubber sheet was then left in a drying oven at approximately 150° C. for approximately 30 minutes in order to dry the urethane rubber sheet and advance the crosslinking reaction. Next, a cover film plate and the urethane rubber sheet on which the conductor and the electrode were formed were set on the printing machine. The cover film coating was then placed on the plate, whereupon the squeegee was moved on the plate in a scan-like manner to print a cover film on the surface of the urethane rubber sheet. The urethane rubber sheet was then left in a drying oven at approximately 150° C. for approximately 30 minutes in order to dry the urethane rubber sheet and advance the crosslinking reaction.

Thus, the conductor and the electrode were formed on the surface of the urethane rubber sheet and the cover film was formed on the same surface so as to cover the conductor and the electrode. The conductor and the electrode were then formed similarly on the back of the urethane rubber sheet, whereupon the cover film was formed on the same surface so as to cover the conductor and the electrode.

Figure 13:
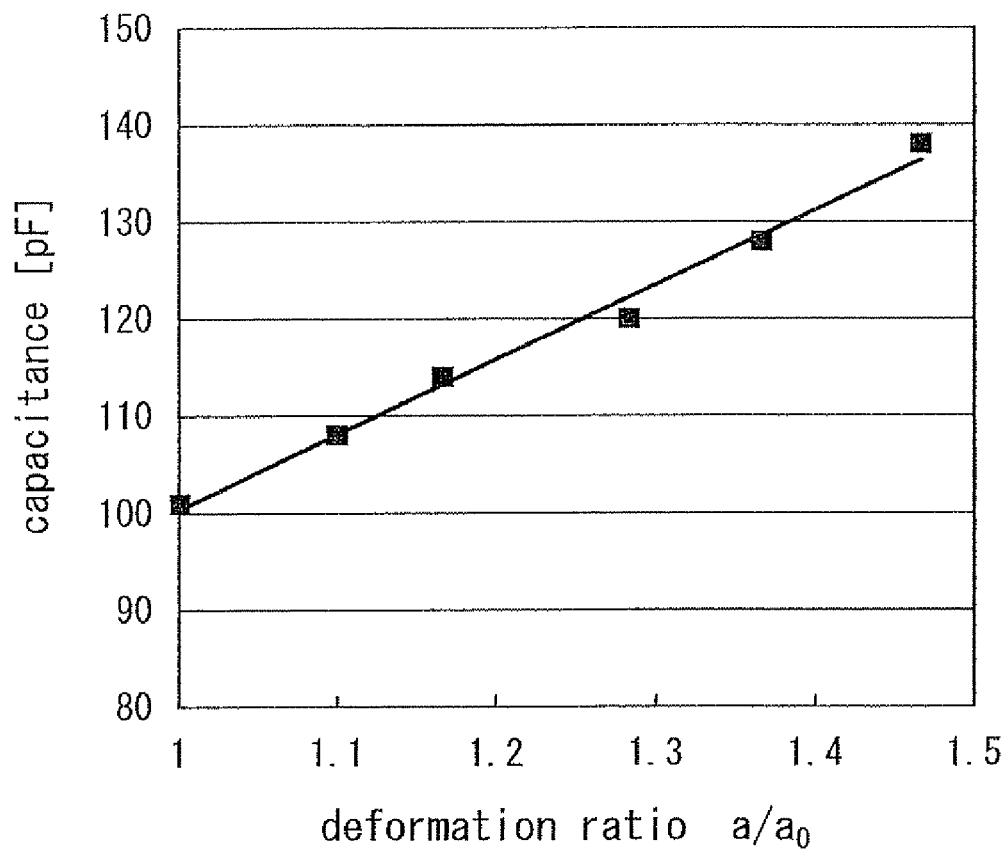
FIG. 13 is a graph showing capacitance variation relative to elongation deformation in a sensor unit of the capacitive sensor according to the first embodiment.

Next, a method of measuring capacitance variation relative to elongation deformation will be described. A pair of electrode portions (a sensor unit) from among the three pairs of electrodes formed on the capacitive sensor 4 was measured. The both ends of the sensor unit in a longitudinal direction were gripped by a jig to elongate the sensor unit. Capacitance variation during the elongation was then measured. FIG. 13 shows capacitance variation relative to a deformation ratio. Here, the deformation ratio is a ratio ($a/a_0$) of a length a of the electrode after elongation in the longitudinal direction (elongation direction) to an initial length $a_0$ of the electrode.

(Test Results)

As shown in FIG. 13, the capacitance increased linearly relative to the deformation ratio. In other words, the capacitance increased as the elongation amount increased. Moreover, the conductors and the electrodes were not disconnected even when the sensor unit was elongated to the deformation ratio of 1.5 (by approximately 50%). It was therefore confirmed that the capacitive sensor according to the present invention possesses stretchability and can detect deformation accurately.

(2) Next, a surface pressure measurement test performed on the capacitive sensor 1 according to the third embodiment described above (see FIGS. 6 and 7) will be described.

(Test Method)

The surface area of the portions of the sensor main body 2 in which the surface side electrodes 01X to 16X and the back side electrodes 01Y to 16Y were arranged was set at 552 cm². A weight pressing the sensor main body 2 had a rectangular parallelepiped shape. The surface area of the weight pressing the sensor main body 2 (a load application surface area) was set at 324 cm², 180 cm², and 149 cm². Variation in the electrostatic capacity obtained from the detection portions A0101 to A1616 when the load was increased in each of three patterns of the load application surface area was then observed.

(Test Results)

Figure 14:
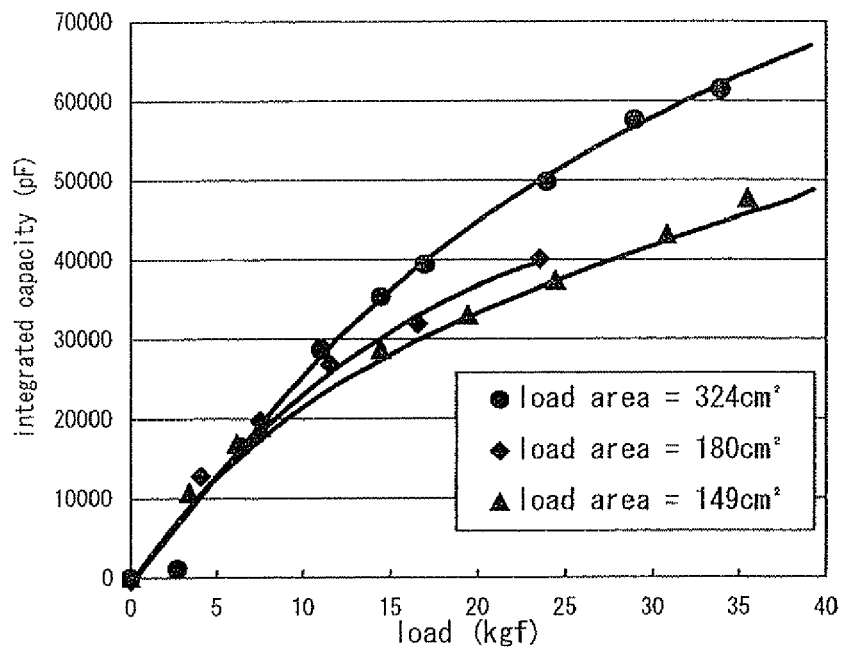
FIG. 14 is a graph showing a relationship between a load and an integrated value of electrostatic capacity in the capacitive sensor according to the third embodiment.

FIG. 14 is a graph showing a relationship between a load and an integrated value of electrostatic capacity. As is evident from FIG. 14, regardless of whether the load application surface area is 324 cm², 180 cm², or 149 cm², the integrated value of electrostatic capacity (=a value obtained by integrating the electrostatic capacity obtained from the detection portions A0101 to A1616) increases as the load increases. In other words, it can be seen that the total load applied to the sensor main body 2 by the weight is proportional to the integrated value of electrostatic capacity.

Figure 15:
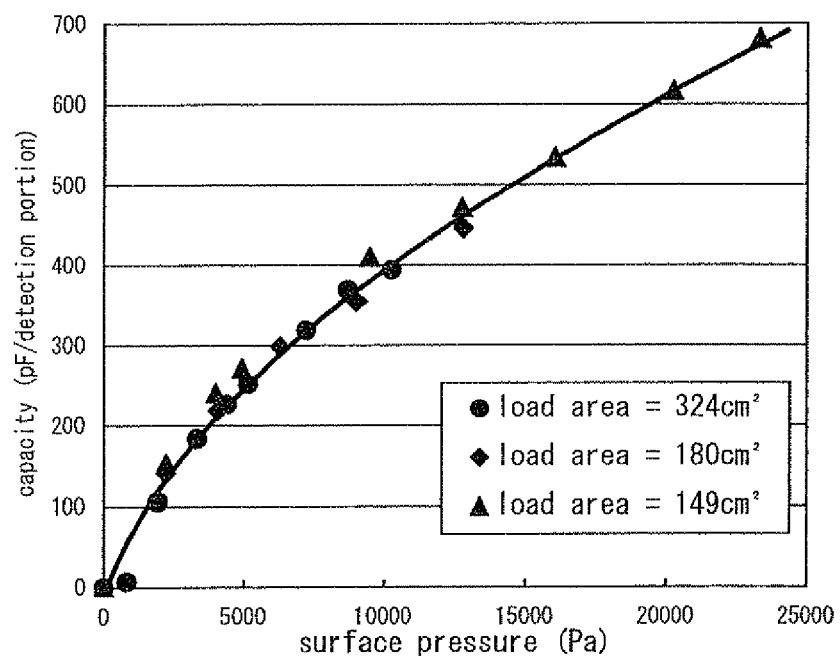
FIG. 15 is a graph showing a relationship between a surface pressure and an electrostatic capacity in the capacitive sensor.

FIG. 15 is a graph showing a relationship between the surface pressure and the electrostatic capacity. As is evident from FIG. 15, regardless of whether the load application surface area is 324 cm², 180 cm², or 149 cm², the electrostatic capacity (=the respective electrostatic capacity values of the detection portions A0101 to A1616) increases as the surface pressure (=load/load application surface area) increases. It can also be seen that regardless of the magnitude of the load application surface area, the surface pressure is proportional to the electrostatic capacity. It can also be seen from FIG. 15 that the surface pressure can be calculated from the electrostatic capacity.

Figure 16:
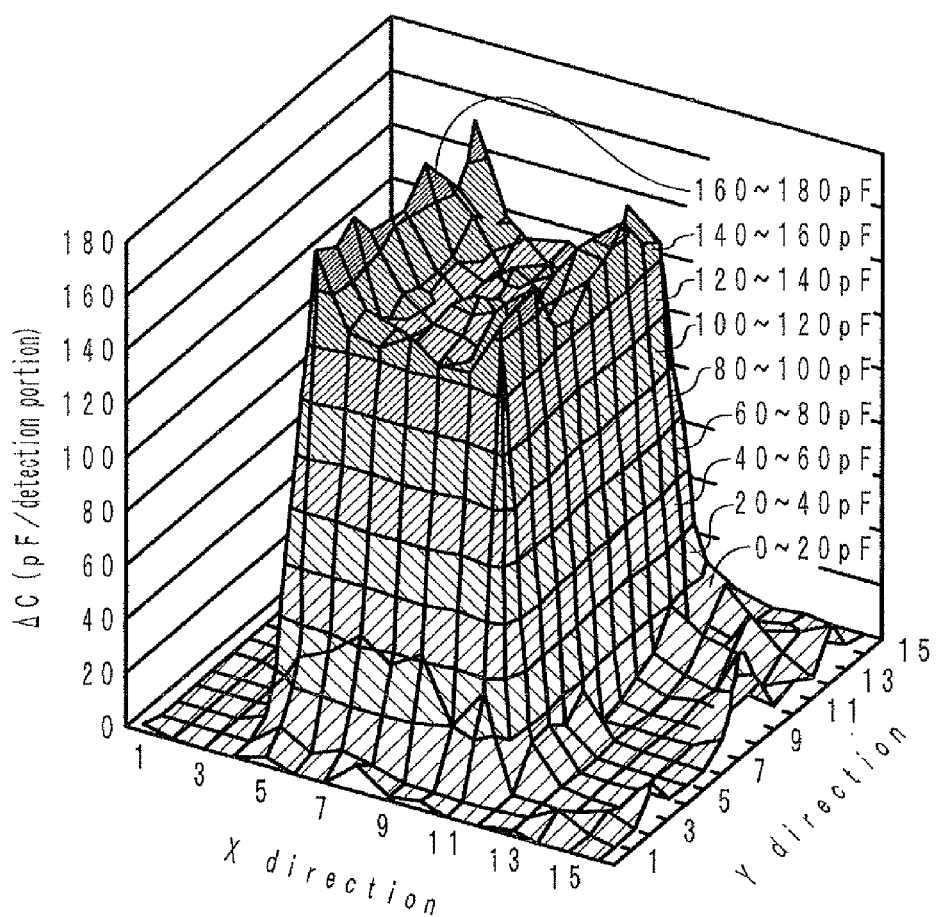
FIG. 16 is a graph showing an electrostatic capacity distribution when a load application surface area of a weight is 149 cm$^2$ and the load is 3.4 kgf.

FIG. 16 is a graph showing an electrostatic capacity distribution when the load application surface area of the weight is 149 cm² and the load is 3.4 kgf. Among all of the 256 detection portions A0101 to A1616, the electrostatic capacity is detected in 70 detection portions. The integrated value of electrostatic capacity is 10728 pF. The surface pressure is 2236 (Pa) [=(3.4 (kgf)×9.8 (N/kgf))/(149×10$^{-4}$ (m²))]. The electrostatic capacity variation (=electrostatic capacity after load application−electrostatic capacity prior to load application) for each of the detection portions A0101 to A1616 is 153.3 (pF/detection portion) [=10728 (pF)/70 (detection portions)]. As is evident from FIG. 16, the electrostatic capacity distribution corresponds to the shape (substantially square) of the load application surface of the weight.

What is claimed is:

1. A capacitive sensor comprising:
    a dielectric layer made of an elastomer and having stretchability; and
    a pair of electrodes arranged via the dielectric layer, wherein
    the pair of electrodes is constituted by an elastomer composition containing the elastomer and conductive fillers,
    in a percolation curve expressing a relationship between a blended amount of the conductive fillers and an electric resistance in the elastomer composition, the blended amount (critical volume fraction: φc) of the conductive fillers at a first polarity change point at which the electric resistance decreases to cause a transition between insulator and conductor is 25 vol % or less,
    the pair of electrodes is expandable and contractible in accordance with a deformation of the dielectric layer and exhibits little conductivity variation when the pair of electrodes expands and contracts,
    at least one of the dielectric layer and the electrodes is formed by a printing method using a dielectric layer coating containing a formation component of the dielectric layer or an electrode coating containing a formation component of the electrode, and
    the capacitive sensor detects a deformation on the basis of an electrostatic capacity variation between the pair of electrodes, and has stretching flexibility.

2. The capacitive sensor according to claim 1, further comprising stretchable conductors connected respectively to the pair of electrodes, wherein each of the conductors contains an elastomer and conductive particles filled into the elastomer, has a smaller electric resistance than the electric resistance of the electrodes, and is formed by the printing method using a conductor coating containing a formation component of the conductor.

3. The capacitive sensor according to claim 2, wherein the pair of electrodes and the conductors are printed onto a surface and a back of the dielectric layer.

4. The capacitive sensor according to claim 2, further comprising an insulating layer that is arranged to cover at least one of the electrodes and the corresponding one of the conductors to insulate the electrode and the conductor from the outside.

5. The capacitive sensor according to claim 2, further comprising a pair of elastic substrates arranged via the dielectric layer, wherein
    the electrode that contacts a surface of the dielectric layer and the corresponding conductor are printed onto a back of one of the elastic substrates, and the electrode that contacts a back of the dielectric layer and the corresponding conductor are printed onto a surface of the other elastic substrate.

6. The capacitive sensor according to claim 1, wherein the conductive fillers constituting the pair of electrodes are formed from a carbon material.

7. A capacitive sensor comprising:
an integrally stretchable sensor main body including
a dielectric layer made of an elastomer,
at least one belt-shaped surface side electrode provided on a surface side of the dielectric layer, the surface side electrode being formed to include an elastomer and conductive fillers filled into the elastomer and including a surface side connection portion,
at least one belt-shaped back side electrode provided on a back side of the dielectric layer, the back side electrode being formed to include an elastomer and conductive fillers filled into the elastomer and including a back side connection portion,
a plurality of detection portions formed by an intersection between the surface side electrode and the back side electrode when seen from a surface-back direction,
a surface side conductor that is connected to the surface side connection portion, formed to include an elastomer and conductive particles filled into the elastomer, and has a smaller electric resistance than the electric resistance of the surface side electrode, and
a back side conductor that is connected to the back side connection portion, formed to include an elastomer and conductive particles filled into the elastomer, and has a smaller electric resistance than the electric resistance of the back side electrode; and
a calculation portion that is electrically connected to the surface side conductor and the back side conductor, separates an electric resistance corresponding to a distance from the surface side connection portion of the surface side electrode to each of the detection portions and the electric resistance corresponding to a distance from the back side connection portion of the back side electrode to each of the detection portions from an impedance detected from the surface side conductor and the back side conductor, extracts an electrostatic capacity of the each detection portion, and calculates a surface pressure distribution on the sensor main body from the electrostatic capacity of the each detection portion.

8. The capacitive sensor according to claim 7, wherein the calculation portion calculates a total load applied to the sensor main body by integrating the electrostatic capacity of each of the plurality of detection portions.

9. The capacitive sensor according to claim 7, wherein the surface side electrode is arranged in a plurality of rows, the back side electrode is arranged in a plurality of rows, and
the plurality of surface side electrodes and the plurality of back side electrodes are arranged substantially orthogonally to each other when seen from the surface-back direction.

10. The capacitive sensor according to claim 7, wherein the surface side electrode and the surface side conductor are printed onto a surface of the dielectric layer, and
the back side electrode and the back side conductor are printed onto a back of the dielectric layer.

11. The capacitive sensor according to claim 7, wherein the sensor main body further includes:
a surface side insulating cover layer that is printed over the surface side electrode and the surface side conductor either directly or indirectly so as to insulate the surface side electrode and the surface side conductor from the outside; and
a back side insulating cover layer that is printed over the back side electrode and the back side conductor either directly or indirectly so as to insulate the back side electrode and the back side conductor from the outside.

12. The capacitive sensor according to claim 7, wherein the sensor main body further includes a tubular insulating tube member that insulates an interior and an exterior of the insulating tube member,
the dielectric layer is housed in the insulating tube member,
the surface side electrode and the surface side conductor are printed onto an inner surface of the insulating tube member in a portion facing the surface of the dielectric layer, and
the back side electrode and the back side conductor are printed onto the inner surface of the insulating tube member in a portion facing the back of the dielectric layer.

13. The capacitive sensor according to claim 7, wherein a surface resistance between both longitudinal ends of at least one of the surface side electrode and the back side electrode is 100 k$\Omega$ or less.

14. The capacitive sensor according to claim 7, wherein the conductive fillers constituting the surface side electrode and the back side electrode are formed from one or more materials selected from conductive carbon black, a carbon nanotube, a derivative of a carbon nanotube, graphite, and conductive carbon fiber.

* * * * *